US011401494B2

(12) United States Patent
Binninger

(10) Patent No.: US 11,401,494 B2
(45) Date of Patent: Aug. 2, 2022

(54) CELL PROCESSING SYSTEM AND METHOD WITH FILL OPTIONS

(71) Applicant: Fenwal, Inc., Lake Zurich, IL (US)

(72) Inventor: Steven C. Binninger, Evanston, IL (US)

(73) Assignee: FENWAL, INC., Lake Zurich, IL (US)

( * ) Notice: Subject to any disclaimer, the term of this patent is extended or adjusted under 35 U.S.C. 154(b) by 237 days.

(21) Appl. No.: 15/703,067

(22) Filed: Sep. 13, 2017

(65) Prior Publication Data

US 2018/0072977 A1    Mar. 15, 2018

Related U.S. Application Data

(60) Provisional application No. 62/394,388, filed on Sep. 14, 2016.

(51) Int. Cl.
| | | |
|---|---|---|
| *C12M 3/00* | (2006.01) | |
| *A61M 1/00* | (2006.01) | |
| *C12M 1/00* | (2006.01) | |
| *A61M 1/02* | (2006.01) | |
| *A61M 1/26* | (2006.01) | |

(52) U.S. Cl.
CPC .......... *C12M 29/04* (2013.01); *A61M 1/0209* (2013.01); *C12M 23/14* (2013.01); *C12M 23/26* (2013.01); *C12M 23/40* (2013.01); *C12M 29/00* (2013.01); *A61M 1/0231* (2014.02); *A61M 1/265* (2014.02)

(58) Field of Classification Search
CPC ....... C12M 23/14; C12M 29/00; C12M 23/40
See application file for complete search history.

(56) References Cited

U.S. PATENT DOCUMENTS

| | | | |
|---|---|---|---|
| 5,053,121 A | 10/1991 | Schoendorfer et al. | |
| 5,194,145 A | 3/1993 | Schoendorfer | |
| 5,789,147 A | 8/1998 | Rubinstein et al. | |
| 5,840,502 A | 11/1998 | Van Vlasselaer | |
| 5,927,560 A * | 7/1999 | Lewis ................. | B05C 11/1034 222/263 |
| 6,464,624 B2 | 10/2002 | Pages | |
| 6,709,378 B2 | 3/2004 | Nishimura et al. | |
| 6,716,151 B2 | 4/2004 | Panzani et al. | |
| 6,733,433 B1 | 5/2004 | Fell | |
| 7,011,852 B2 | 3/2006 | Sukavaneshvar et al. | |

(Continued)

FOREIGN PATENT DOCUMENTS

| | | |
|---|---|---|
| EP | 1254675 | 11/2002 |
| WO | WO2012/125457 | 9/2012 |
| WO | WO2012/125470 | 9/2012 |

OTHER PUBLICATIONS

European Patent Office, Partial European Search Report, counterpart EP Appl. No. 17190829.6, dated Jan. 15, 2018.
U.S. Appl. No. 15/702,894, filed Sep. 13, 2017.

*Primary Examiner* — Nathan A Bowers
(74) *Attorney, Agent, or Firm* — Cook Alex Ltd.

(57) ABSTRACT

A variety of fill options is provided for a cell processing system. Certain options relate to a syringe assembly that receives a product directly from a separator. Other options relate to a filling system associated with the cell processing system, the filling system comprising one or more filling stations, each with at least one container, that receive product from a product container associated with the cell processing system.

20 Claims, 15 Drawing Sheets

(56) References Cited

U.S. PATENT DOCUMENTS

| | | |
|---|---|---|
| 7,179,391 B2 | 2/2007 | Leach et al. |
| 7,291,450 B2 | 11/2007 | Sowemimo-Coker et al. |
| 7,364,657 B2 | 4/2008 | Mandrusov et al. |
| 7,374,678 B2 | 5/2008 | Leach et al. |
| 8,101,077 B2 | 1/2012 | Sukavaneshvar et al. |
| 8,439,889 B2 | 5/2013 | Sano |
| 8,556,793 B2 | 10/2013 | Foley et al. |
| 8,808,551 B2 | 8/2014 | Leach et al. |
| 8,961,787 B2 | 2/2015 | Wood et al. |
| 8,986,185 B2 | 3/2015 | Del Vecchio |
| 9,033,948 B2 | 5/2015 | Payrat et al. |
| 9,352,021 B2 | 5/2016 | Hanna et al. |
| 9,452,254 B2 | 9/2016 | Kimura et al. |
| 9,459,186 B2 | 10/2016 | Mastromatteo et al. |
| 9,603,986 B2 | 3/2017 | Kusters et al. |
| 9,717,842 B2 | 8/2017 | Min et al. |
| 9,907,899 B2 | 3/2018 | Kim |
| 2008/0171951 A1 | 7/2008 | Fell |
| 2010/0047914 A1* | 2/2010 | Peyman .............. G01N 33/6863 436/86 |
| 2011/0124106 A1 | 5/2011 | Froman et al. |
| 2013/0092630 A1 | 4/2013 | Wegener |
| 2013/0155133 A1* | 6/2013 | Ikeda .................... B05B 13/04 347/7 |
| 2014/0357465 A1 | 12/2014 | Barry, Jr. et al. |
| 2015/0060363 A1 | 3/2015 | Kusters et al. |
| 2015/0080204 A1 | 3/2015 | Kassis |
| 2015/0122997 A1 | 5/2015 | Sandford |
| 2016/0252434 A1 | 9/2016 | Smith et al. |
| 2017/0262601 A1 | 9/2017 | Binninger |
| 2017/0340783 A1 | 11/2017 | Wegener et al. |
| 2018/0015418 A1 | 1/2018 | Binninger et al. |

* cited by examiner

CELL PROCESSING SYSTEM AND METHOD WITH FILL OPTIONS

CROSS-REFERENCE TO RELATED APPLICATIONS

This application claims the benefit of U.S. Provisional Application No. 62/394,388, filed Sep. 14, 2016, which is hereby incorporated herein by reference.

TECHNICAL FIELD

The present disclosure is generally directed to systems and methods for processing a fluid to generate a product, and related systems and methods for filling the product into one or more containers. More particularly, the present disclosure is directed to the processing of biological fluid using a disposable fluid circuit and a reusable processing machine to generate a product, and related systems and methods for filing the product into one or more containers, including end-user containers.

BACKGROUND

The processing of biological fluid such as blood or blood components typically involves using a reusable processing machine ("hardware") and a disposable fluid circuit adapted for mounting or other association with the reusable apparatus. The fluid circuit typically includes (plastic) bags and associated tubing that defines a flow path through the circuit. The disposable fluid circuit may also include one or more separation devices where the biological fluid/cells can be separated into two or more components, washed or otherwise processed. Separation devices may separate the biological fluid based on centrifugal separation and/or, as described below, membrane separation.

Conventionally, the product is directed into a product container, such as a flexible walled bag. At the time of use, the product may be removed from the bag via a port or port assembly. In particular, one or more syringes may be connected to the port, and then the product from the bag is drawn into the syringe. Consequently, cells may be left in the product bag and not transferred to the syringes. Further, the method provides the potential for contamination of the product in the syringe if proper sterilization protocols are not used.

SUMMARY

In one aspect, a cell processing system includes a processor connectable to a source container filled with a biological fluid. The processor, in turn, includes a separator configured to separate the biological fluid from the source container into at least two streams, and at least one syringe assembly configured to receive one of the at least two streams. The at least one syringe assembly includes a syringe having a barrel and a plunger that defines a volume that is in fluid communication with the one of the at least two streams.

According to another aspect, a processing and filling system includes a cell processing system and a filling system. The cell processing system includes a processor connectable to a source container filled with a biological fluid. The processor, in turn, includes a separator configured to separate the biological fluid from the source container into at least two streams. The filling system is associated with the cell processing system and proximate to the cell processing system, and includes at least one filling station in fluid communication with the cell processing system, the filing station including at least one container in selective fluid communication with the cell processing system, and a pump configured to transfer a product from the cell processing system to the at least one filling station.

According to a further aspect, a processing and filling system includes a cell processing system and a filling system. The cell processing system includes a first disposable circuit connectable to a source container filled with a biological fluid and reusable hardware including a pump. The first disposable circuit and the reusable hardware define a separator configured to separate the biological fluid from the source container into at least two streams, and a product container configured to receive one of the at least two streams. The filling system includes a second disposable circuit connectable to the product container and the reusable hardware. The second disposable circuit and reusable hardware define at least one filling station, the filing station including at least one container in selective fluid communication with the product container, and the pump of the reusable hardware is configured to transfer a product from the product container to the at least one filling station.

BRIEF DESCRIPTION OF THE FIGURES

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

DETAILED DESCRIPTION

Figure 1:
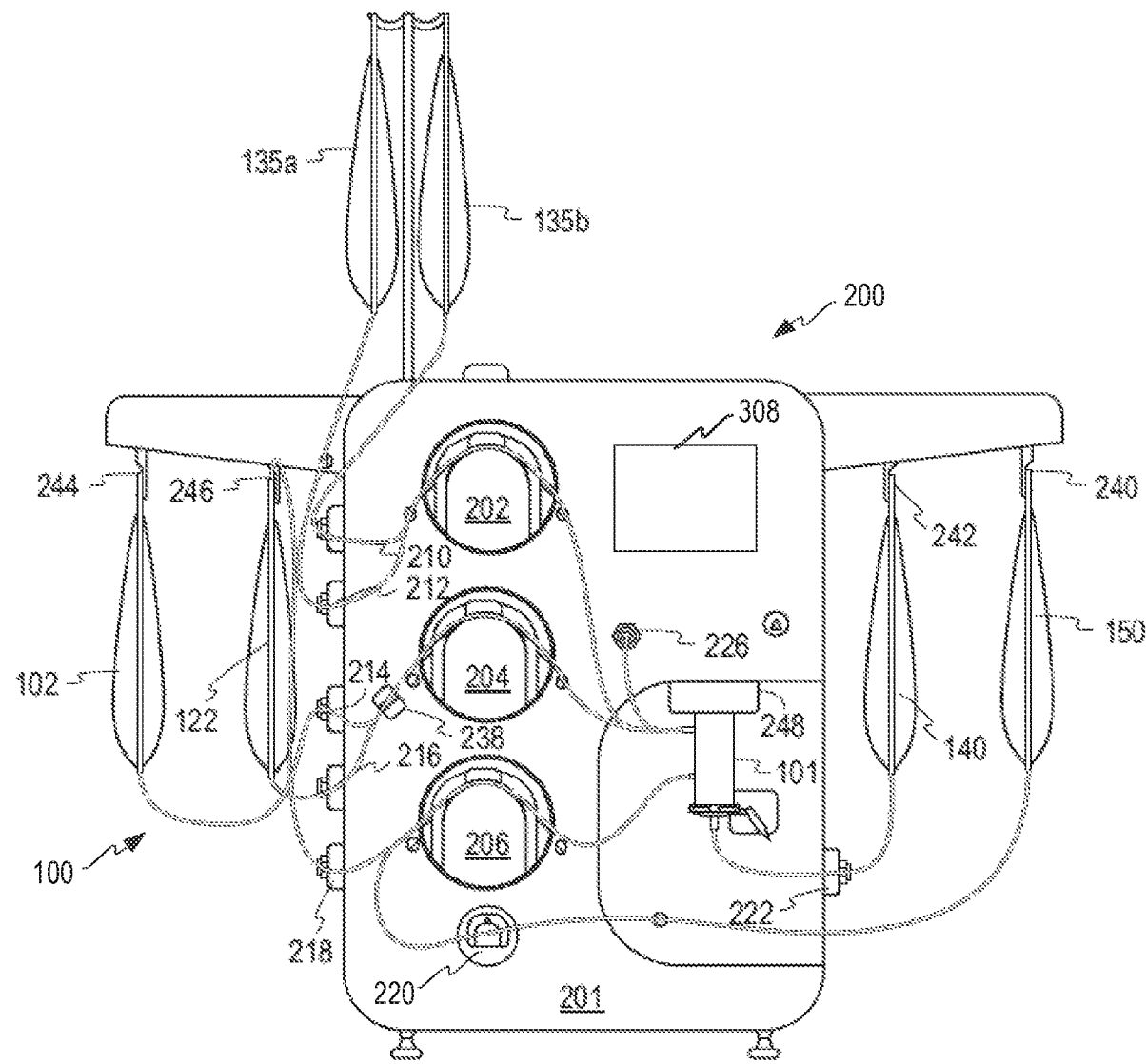
FIG. 1 is a frontal view of a reusable cell processing apparatus with a disposable fluid circuit loaded thereon.
Figure 2:
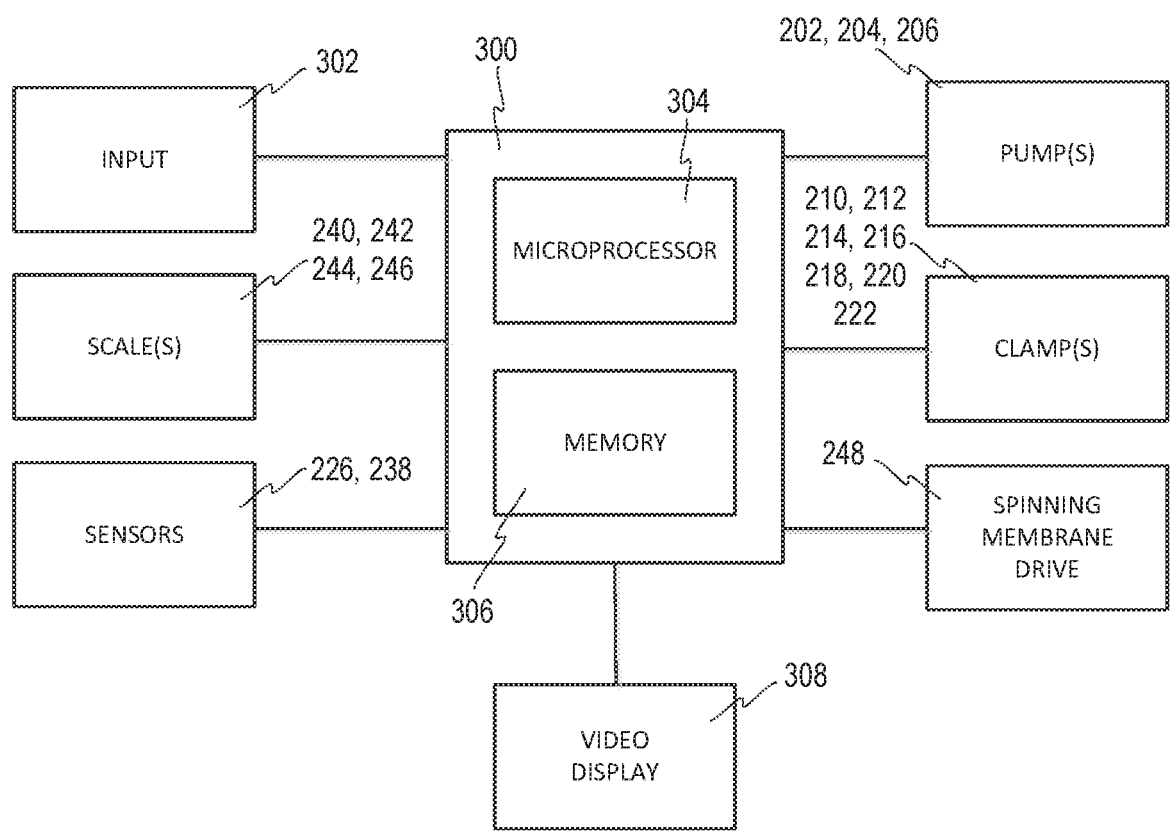
FIG. 2 is a schematic view of the control circuitry of the apparatus of FIG. 1.

As illustrated in FIGS. 1 and 2, a cell processing system includes a processor 100, 200 to receive a biological fluid to be processed, a control unit (or controller) 300 coupled to the processor, the controller 300 configured to operate the processor 100, 200 according to a procedure or process. According to the embodiments described herein, the cell processing system may be used in conjunction with a number of fill options. For example, the embodiments of the cell processing system may be used with a product container that permits the product generated by the cell processing system to be filled into a container that can be used directly by an end user (i.e., an end-user container). Alternatively, the cell processing system may be used with or as a filling system to distribute the product from a product container into a plurality of other containers for storage, shipment, or both after processing of the biological fluid.

As explained in detail below, the processor 100, 200 may include a disposable processing fluid circuit 100 (see also FIGS. 3, 5, 8 and 9) and reusable hardware 200 (see also FIG. 4). According to the illustrated embodiments, the disposable fluid circuit 100 may include a spinning membrane 101, at least one container 102, 122, 135a, 135b, 140, 150 or assembly 602, 702 (of which at least containers 102, 135a, 135b may be initially separate and then connected to the remainder of the circuit 100 at the time of processing), and tubing 106, 120, 128, 132a, 132b, 162, 166, 168 connecting the spinning membrane 101 and the one or more containers 102, 122, 135a, 135b, 140, 150 and/or assemblies 602, 702. As is also illustrated, the reusable hardware 200 may include at least one drive 248 to spin the spinning membrane 101, at least one scale 240, 242, 244, 246 to weigh the at least container 102, 122, 140, 150 or assembly 602, 702 and contents thereof, and at least one pump 202, 204, 206 to receive the tubing 162, 166, 168 and pump fluid through the tubing 162, 166, 168 by peristaltic action, for example, although other types of pumps and pumping action may be used. The controller 300 may, according to the embodiments, include a programmable microprocessor 304, which microprocessor 304 may be coupled to the at least one input 302 and may be programmed to operate the processor according to a process.

The processor 100, 200 may be used in conjunction with a filling system or apparatus, which filing system may include a pump (which may in the form of a peristaltic pump) and one or more filling stations. Each filing station may include a container and one or more of a mechanism that limits fluid flow into the container (e.g., a clamp or valve), a sensor that can be used to monitor the fluid flowing into the container, and a scale that can be used to determine the amount of fluid flowing into the container. Given that the processor 100, 200 includes a number clamps and scales, as explained herein, the processor 100, 200 may be controlled by the controller 300 to operate as a filling system as well.

While the foregoing discussion references embodiments in the form of a cell processing system, other systems may incorporate this technology as well. These systems may share the technical challenges faced by the aforementioned cell processing system, and incorporation of the technology may provide similar advantages. For example, a separation system, more particularly a filtration system, or even more particularly a microfiltration system, also may include a processor to receive a fluid to be processed and a controller. Further, certain embodiments of such a processor may include a disposable fluid circuit (which circuit may include a membrane used for filtration) and reusable hardware, and the controller may be configured to operate the processor.

Having thus described the system and method in general terms, the details of the system and method are described in detail. Because the filling options discussed herein are used in conjunction with a cell processing system, and may make use of or directly connect to the reusable and disposable components of the cell processing system, the cell processing system is described herein, to provide context for the further discussion of the filling options discussed below.

As mentioned above, the cell processing systems disclosed herein typically include a reusable separation apparatus and one or more disposable processing circuits adapted for association with the reusable apparatus, which apparatus and circuit(s) define the processor. The reusable separation apparatus may be any apparatus that can provide for the automated processing of biological fluid. "Biological fluid" includes without limitation blood and blood components, and "cell" or "biological cell" includes without limitation blood cells, such as red cells, white cells and platelets. By "automated," it is meant that the apparatus can be programmed to carry out the processing steps of a biological fluid processing method without substantial operator involvement. Of course, even in the automated system of the present disclosure, it will be understood that operator activity may be involved, including the loading of the disposable fluid circuits and entering processing parameters. Additional manual steps may be required as well. However, the reusable apparatus can process biological fluid through the disposable circuit(s) described below without substantial operator intervention.

Figure 6:
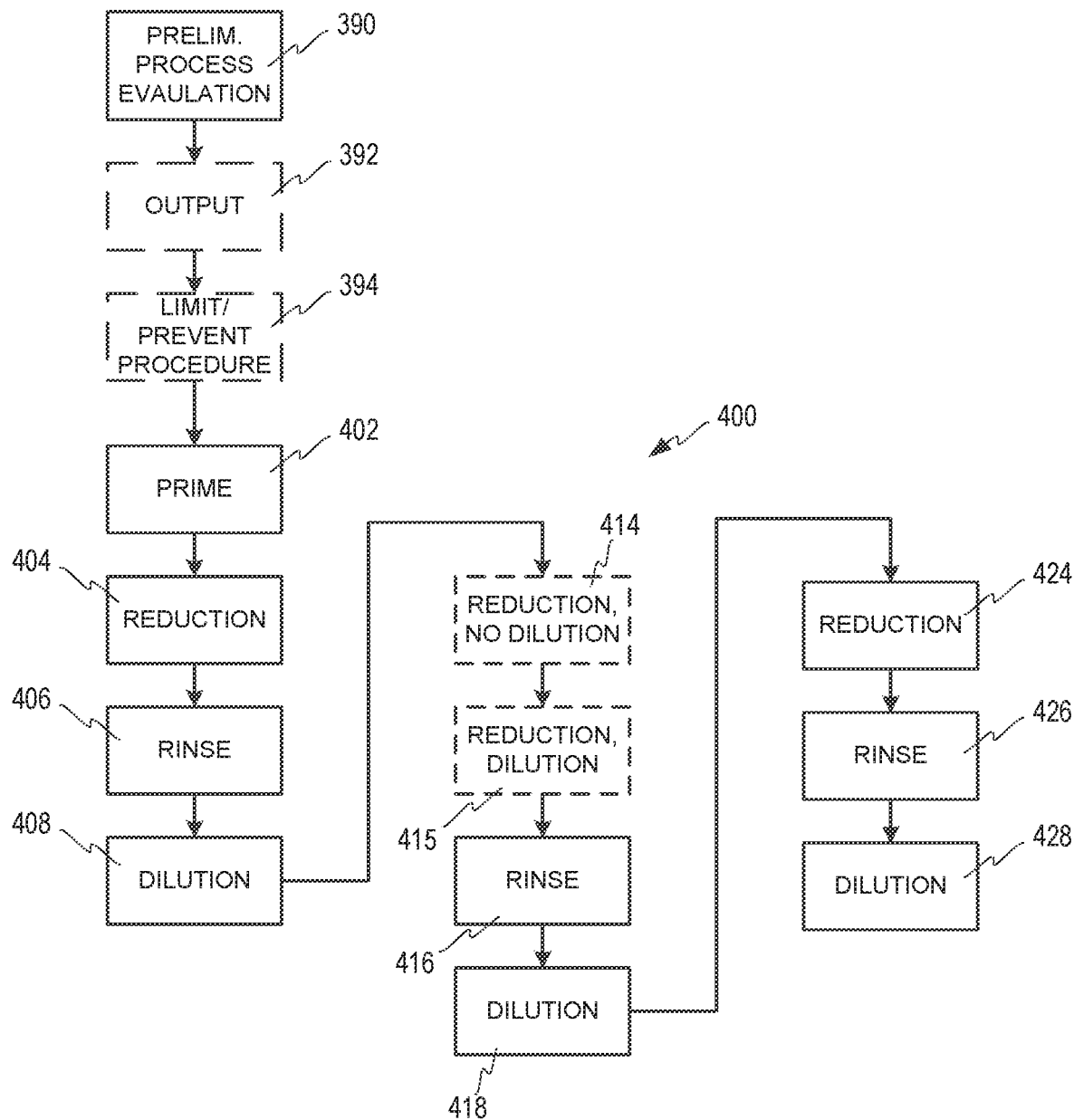
FIG. 6 is a flowchart of one embodiment of a method of operating a reusable cell processing apparatus with a disposable fluid circuit loaded thereon, such as is illustrated in FIG. 1, to process a biological fluid.

The illustrated processing apparatus is typically capable of effecting the separation of a biological fluid that includes biological cells into two or more components or fractions. Thus, the reusable apparatus may generate conditions that allow for the separation of a biological fluid into selected components or fractions. One preferred machine for separating biological fluid into its constituent components or fractions uses a spinning porous membrane. An example of such machine is the Autopheresis C® sold by Fenwal, Inc. of Lake Zurich, Ill., which is an affiliate of Fresenius Kabi AG of Bad Homburg, Germany. A detailed description of a spinning membrane may be found in U.S. Pat. No. 5,194,145 to Schoendorfer, which is incorporated by reference herein in its entirety, and in International (PCT) Application No. PCT/US2012/028492, filed Mar. 9, 2012, the contents of which are also incorporated herein in their entirety. In addition, systems and methods that utilize a spinning porous membrane are also disclosed in U.S. Provisional Patent Application No. 61/537,856, filed on Sep. 22, 2011, and International (PCT) Application No. PCT/US2012/028522, filed Mar. 9, 2012, the contents of each are incorporated herein by reference. The references identified above describe a membrane-covered spinner having an interior collection system disposed within a stationary shell. While a detailed discussion of the separation device is beyond the scope of this application, the spinning membrane separation device is shown in FIGS. 6, 7(a)-7(b) of the reference cited and is discussed below in general terms. In another embodiment, the reusable apparatus may generate a centrifugal field to effect separation.

Figure 3:
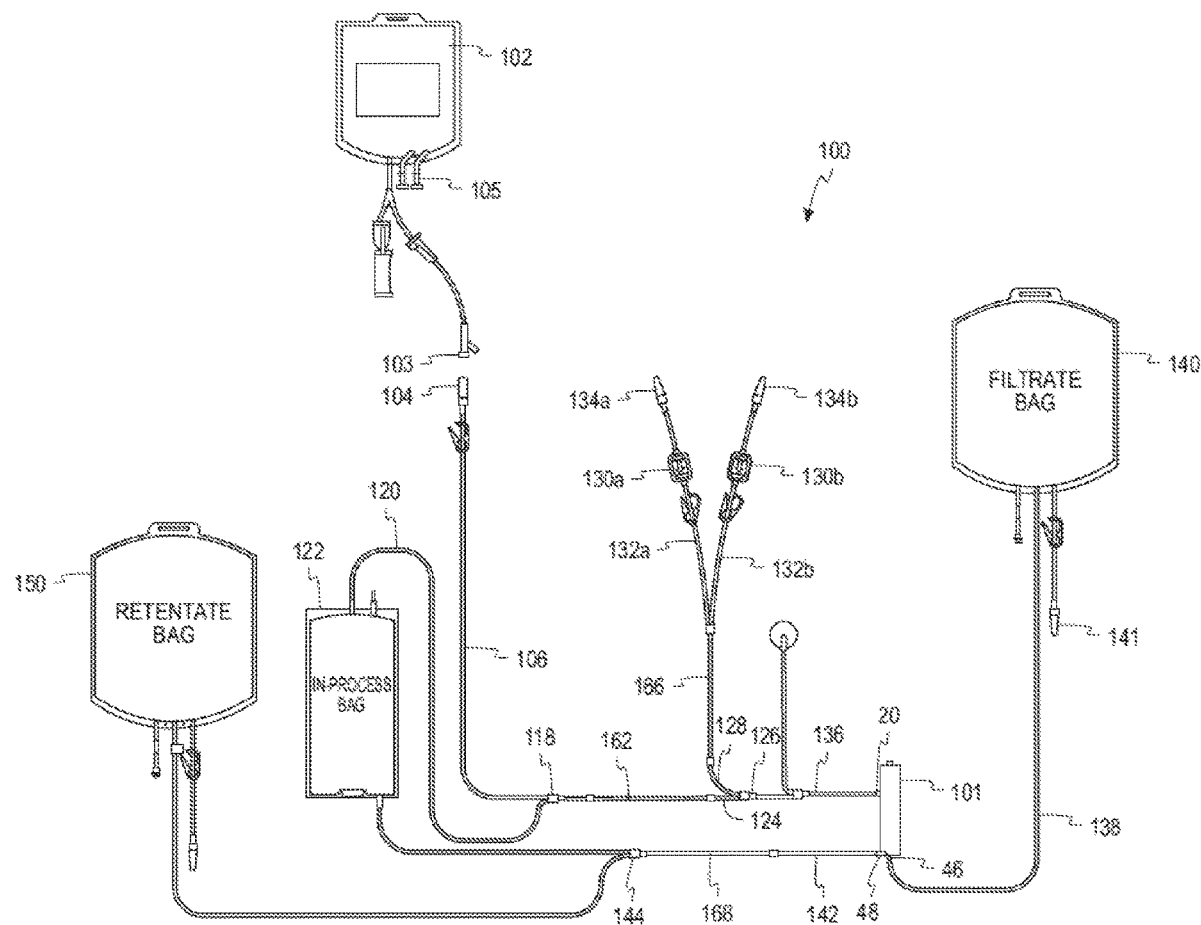
FIG. 3 is a schematic view of one embodiment of a disposable fluid circuit useful in the systems and methods described herein.

Turning now to FIG. 3, the systems described herein include at least one disposable fluid circuit 100 for use in the processing of biological fluid. While the circuits described herein may be used as stand-alone circuits, more preferably, at least two or more disposable fluid circuits are used in combination and in series for the separation, washing, volume reduction and/or other processing of a biological fluid. Circuit 100 may include an integrated separation device, such as, but not limited to, the spinning membrane 101 described above. Circuit 100 may also include waste container 140, product container 150, and in-process container 122. Disposable fluid circuits of the type described below may further include sampling assemblies (not shown) for collecting samples of source biological fluid, "final" product, or other intermediate products obtained during the biological fluid processing.

As will be seen in the Figures and described in detail below, the disposable fluid processing circuits include tubing that defines flow paths throughout the circuits, as well as access sites for sterile or other connection to containers of processing solutions, such as wash solutions, treating agents, or sources of biological fluid. As shown in FIG. 3, the tubing of circuit 100 includes spaced tubing segments identified by reference numerals 162, 166, 168. The tubing segments are provided for mating engagement with the peristaltic pumps 202, 204, 206 of the reusable hardware apparatus 200 discussed below. The containers and the plastic tubing are made of conventional medical grade plastic that can be sterilized by sterilization techniques commonly used in the medical field such as, but not limited to, radiation or autoclaving. Plastic materials useful in the manufacture of containers and of the tubing in the circuits disclosed herein include plasticized polyvinyl chloride). Other useful materials include acrylics. In addition, certain polyolefins may also be used.

As will be apparent from the disclosure herein, source containers may be attached in sterile fashion to the circuit 100. Source containers 102 for connection to one disposable circuit may be the product containers 150 of another circuit used in an earlier step of the overall method of processing. Alternatively, the contents of a product container 150 may be further processed or separated and then transferred in sterile fashion to the source container 102 of a later-in-series fluid circuit.

The biological cell suspension to be washed or otherwise treated is typically provided in a source container 102, shown in FIG. 3 as (initially) not connected to the disposable set. As noted above, source container 102 may be attached (in sterile fashion) at the time of use. Source container 102 has one or more access sites 103, 105, one of which may be adapted for (sterile) connection to fluid circuit 100 at docking site 104. Preferably, source containers may be attached in a sterile manner by employing sterile docking devices, such as the BioWelder, available from Sartorius AG, or the SCD IIB Tubing Welder, available from Terumo Medical Corporation. A second access port 105 may also be provided for extracting fluid from the source container 102.

As further shown in FIG. 3, tubing segment 106 extends from docking site 104 and is connected to further downstream branched-connector 118. Branched-connector 118 communicates with tubing 106 and tubing 120, which provides a fluid flow path from "in-process" container 122, described in detail below. Tubing segment 124 extends from branched-connector 118 and is joined to a port of further downstream branched-connector 126. A separate flow path defined by tubing 128 is also connected to a port of branched-connector 126, In accordance with the fluid circuit of FIG. 3, one or more containers of wash or other processing/treating solution may be attached (or pre-attached) to set 100. As shown in FIG. 3, tubings 132a, 132b (defining a flow path) preferably include and terminate in an access site such as spike connectors 134a, 134b. Access sites 134a, 134b are provided to establish flow communication with containers 135a, 135b (shown in FIG. 1) of a wash fluid, such as saline or other solution. Tubings 132a, 132b may include in-line sterile barrier filters 130a, 130b for filtering any particulate from a fluid before it enters the flow path leading to second branched-connector 126 and, ultimately separator 101. In one embodiment, the sterile barrier filters 130a, 130b may be 0.2 μm filters. The wash medium or fluid flows from the wash fluid source through tubing segments 132a, 132b where it is filtered by the sterile barrier filters 130a, 130b described above, and then passes through tubing 128 to the input of the branched-connector 126 described above.

Tubing segment 136 defines a flow path connected at one end to branched-connector 126 and to an inlet port 20 of the separator 101. Preferably, in accordance with the present disclosure, separation device 101 is a spinning membrane separator of the type described in U.S. Pat. Nos. 5,194,145 and 5,053,121, which are incorporated by reference, U.S. Provisional Patent Application Ser. No. 61/451,903 and PCT/US2012/028522, also previously incorporated herein by reference.

As shown in FIG. 3 (and described in detail in connection with FIG. 5), the spinning membrane separator 101 has at least two outlet ports. Outlet 46 of separator 101 receives the waste from the wash (i.e., the diluted suspension medium) and is connected to tubing 138, which defines a flow path to waste product container 140. The waste product container 140 includes a further connection port 141 for sampling or withdrawing the waste from within the product container.

Separation device 101 preferably includes a second outlet 48 that is connected to tubing segment 142 for directing the desired biological cell/fluid product to the in-process container(s) 122 or the product container 150. To permit this, the other end of tubing segment 142 is connected to branched-connector 144, which branches into and defines a flow path to one or more in-process containers 122 and a flow path to a "final" product container 150. The product container 150 may also include a sampling assembly (not shown).

Figure 4:
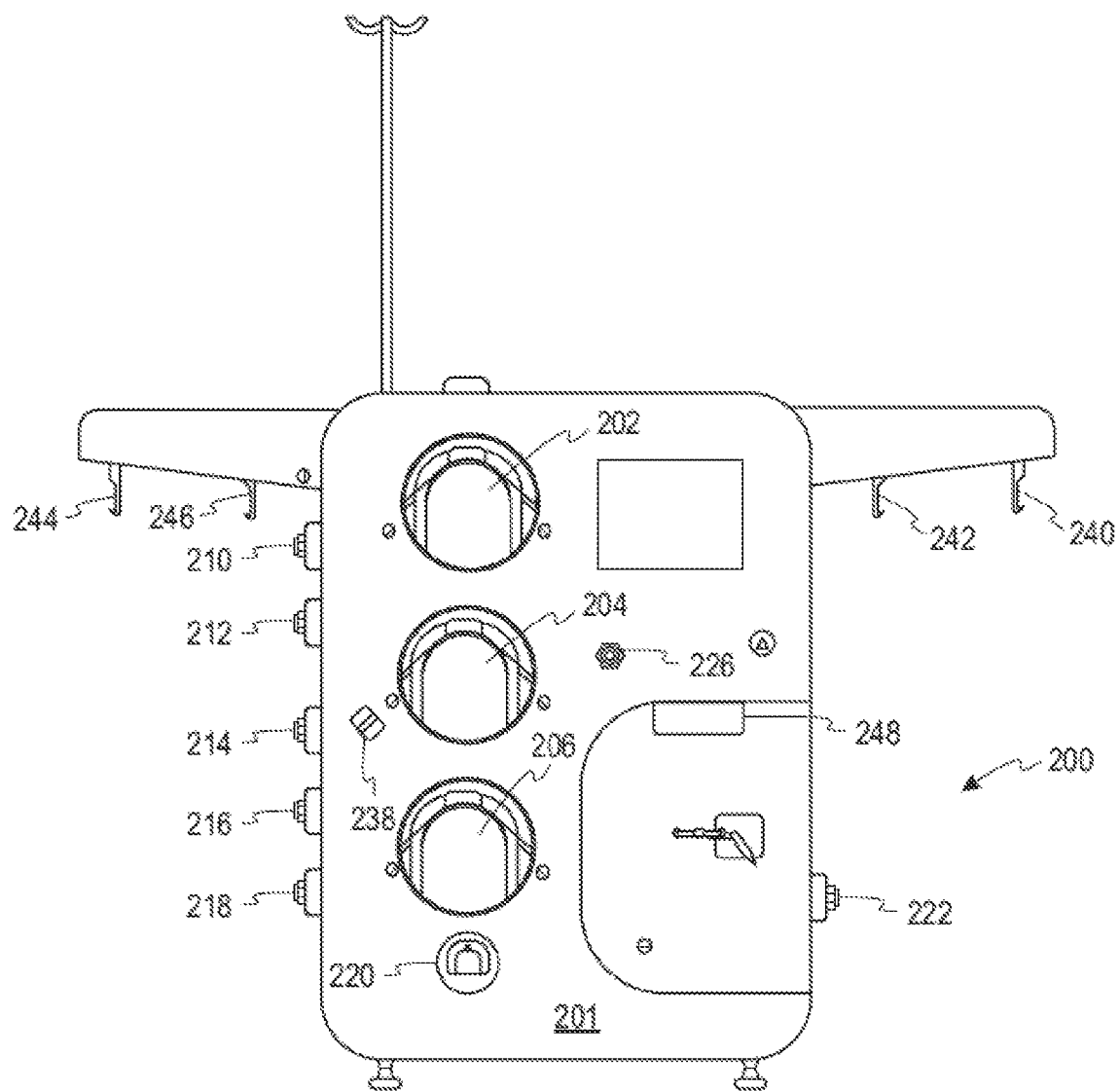
FIG. 4 is a frontal view of the reusable cell processing apparatus.

FIG. 4 shows the front panel 201 of reusable hardware processing apparatus 200, also referred to herein as "hardware". Apparatus 200 may be of compact size suitable for placement on a tabletop of a lab bench and adapted for easy transport. Alternatively, apparatus 200 may be supported by a pedestal that can be wheeled to its desired location. In any event, as shown in FIG. 4, apparatus 200 includes a plurality of peristaltic pumps such as pumps 202, 204 and 206 on front panel 201. Pump segments of the disposable fluid circuit (described above) are selectively associated with peristaltic pumps 202, 204, and 206. The peristaltic pumps articulate with the fluid set of FIG. 3 at the pump segments identified by reference numerals 162, 166, 168 and advance the cell suspension or other fluid within the disposable set, as will be understood by those of skill in the art. Apparatus 200 also includes clamps 210, 212, 214, 216, 218, 220 and 222. The clamps are used to control the flow of the cell suspension through different segments of the disposable set, as described above.

Apparatus 200 also includes several sensors to measure various conditions. The output of the sensors is utilized by device 200 to operate one or more wash or processing cycles. One or more pressure transducer sensor(s) 226 may be provided on apparatus 200 and may be associated with a disposable set 100 at certain points to monitor the pressure during a procedure. Pressure transducer 226 may be integrated into an in-line pressure monitoring site (at, for example, tubing segment 136), to monitor pressure inside separator 101. Air detector sensor 238 may also be associated with the disposable set 100, as necessary. Air detector 238 is optional and may be provided to detect the location of fluid/air interfaces.

Apparatus 200 includes weight scales 240, 242, 244, and 246 from which the final product container 150, waste container 140, the source container 102 and the in-process container 122, respectively, may depend and be weighed. The weights of the bags are monitored by weight sensors and recorded during a washing or other procedure. From measurements of the weight sensors, the device determines whether each container is empty, partially full, or full and controls the components of apparatus 200, such as the peristaltic pumps 202, 204 and 206 and clamps 210, 212, 214, 216, 218, 220 and 222.

Apparatus 200 includes at least one drive unit or "spinner" 248, which causes the indirect driving of the spinning membrane separator 101. Spinner 248 may consist of a drive motor connected and operated by apparatus 200, coupled to turn an annular magnetic drive member including at least a pair of permanent magnets. As the annular drive member is rotated, magnetic attraction between corresponding magnets within the housing of the spinning membrane separator cause the spinner within the housing of the spinning membrane separator to rotate.

Figure 5:
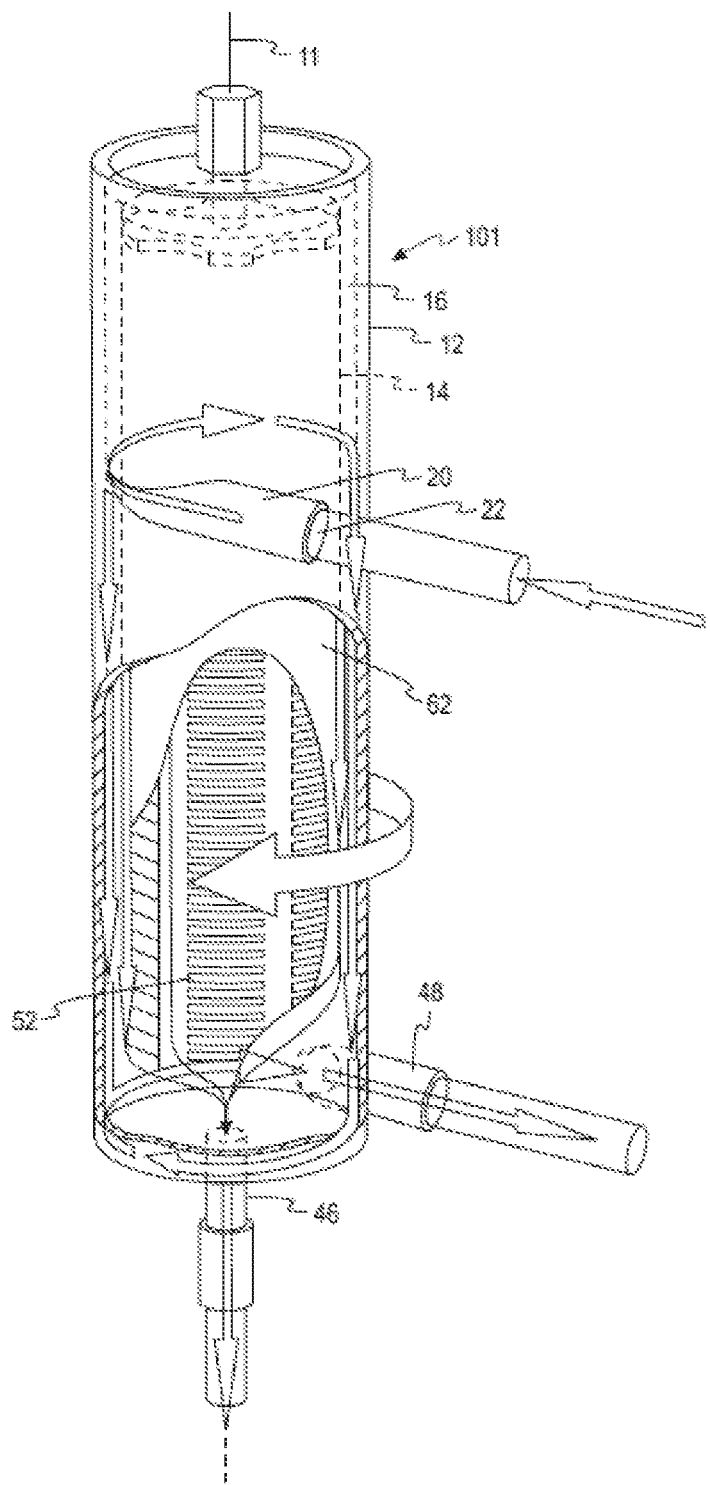
FIG. 5 is a perspective view of a separation/washing device using a spinning membrane.

Turning to FIG. 5, a spinning membrane separation device, generally designated 101, is shown. Such a device 101 forms part of the disposable circuit 100.

Device 101 includes a generally cylindrical housing 12, mounted concentrically about a longitudinal vertical central axis. An internal member 14 is mounted concentric with the central axis 11. Housing 12 and internal member 14 are relatively rotatable. In the preferred embodiment, as illustrated, housing 12 is stationary and internal member 14 is a rotating spinner that is rotatable concentrically within cylindrical housing 12, as shown by the thick arrow in FIG. 5. The boundaries of the flow path are generally defined by gap 16 between the interior surface of housing 12 and the exterior surface of rotary spinner 14. The spacing between the housing and the spinner is sometimes referred to as the shear gap. The shear gap may be approximately 0.02-0.06 inches (0.05-0.15 cm) and may be of a uniform dimension along axis 11, for example, where the axis of the spinner and housing are coincident. The shear gap may also vary circumferentially for example, where the axis of the housing and spinner are offset.

The shear gap also may vary along the axial direction, for example preferably an increasing gap width in the direction. Such a gap width may range from about 0.02 to about 0.075 inches (0.05-0.19 cm). The gap width could be varied by varying the outer diameter of the rotor and/or the inner diameter of the facing housing surface. The gap width could change linearly or stepwise or in some other manner as may be desired. In any event, the width dimension of the gap is preferably selected so that at the desired relative rotational speed, Taylor-Couette flow, such as Taylor vortices, are created in the gap.

Biological fluid is fed from an inlet conduit 20 through an inlet orifice 22, which directs the fluid into the fluid flow entrance region in a path tangential to the circumference about the upper end of the spinner 14. At the bottom end of the cylindrical housing 12, the housing inner wall includes an exit orifice 48.

Cylindrical housing 12 is completed by a bottom end housing terminating in an outlet orifice 46 concentric with the central axis.

In the illustrated embodiment, the surface of the rotary spinner 14 is at least partially, and is preferably substantially or entirely, covered by a cylindrical porous membrane 62. The membrane 62 may have a nominal pore size between 0.8 and 10 microns ($\mu$m), for example. Membranes may be fibrous mesh membranes, cast membranes, track-etched membranes or other types of membranes that will be known to those of skill in the art. For example, in one embodiment, the membrane may have a polyester mesh (substrate) with nylon particles solidified thereon, thereby creating a tortuous path through which only certain sized components pass. In an embodiment, the nylon membrane may have a pore size of approximately 0.8 $\mu$m and a thickness of approximately 150 $\mu$m or greater. Membranes of this type will typically retain all cellular components (e.g., red blood cells, white blood cells) and certain formed blood components, e.g., platelets. In another embodiment, the membrane may be made of a thin (approximately 10 $\mu$m thick) sheet of unsupported polycarbonate, for example, with a pore size of approximately 4.0 $\mu$m. In this embodiment, pores (holes) may be cylindrical and larger than those described above. The pores may be sized to allow small formed components (e.g., platelets, microparticles, etc.) to pass, while the desired cells (e.g., white blood cells and larger red blood cells) are collected.

Having thus described the processor, including disposable circuit 100 and reusable hardware 200, reference is made to FIG. 2 to discuss additional details of the control unit or controller 300. As mentioned above, the controller 300 may include a microprocessor 304 (which, in fact may include multiple physical and/or virtual processors). According to other embodiments, the controller 300 may include one or more electrical circuits designed to carry out the actions described herein. In fact, the controller 300 may include a microprocessor and other circuits or circuitry. In addition, the controller 300 may include one or more memories 306. The instructions by which the microprocessor 304 is programmed may be stored on the memory 306 associated with the microprocessor 304, which memory/memories 306 may include one or ore tangible non-transitory computer readable memories, having computer executable instructions stored thereon, which when executed by the microprocessor 304, may cause the microprocessors 304 to carry out one or more actions as described below.

As is also illustrated in FIG. 2, the controller 300 may be coupled to one or more of the structures described above, for example to receive information (e.g., in the form of signals) from these structures or to provide commands (e.g., in the form of signals) to these structures to control the operation of the structures. As illustrated, the controller 300 may be coupled to the scales 240, 242, 244, 246, the sensors 226, 238 and the at least one input 302 to receive information from those devices. Additionally, the controller 300 may be coupled to the pumps 202, 204, 206, the clamps 210, 212, 214, 216, 218, 220, 222, and the drive 248 to provide commands to those devices to control their operation. It may also be possible that the controller 300 receives information from and provides commands to a given structure, such as one of the structures already mentioned. The controller 300 may be directly electrically connected to these structures to be coupled to them, or the controller 300 may be directly connected to other intermediate equipment that is directly connected to these structures to be coupled to them.

The at least one input 302 may include a number of different devices according to the embodiments described herein. For example, the input 302 could include a keyboard or keypad by which a user may provide information and/or instructions to the controller 300. Alternatively, the input 302 may be a touch screen, such as may be used in conjunction with a video display 308 that is disposed on the front panel 201 of the device 200, the video display 308 also being coupled to the controller 300. The input could also include a reader or scanner, such as a barcode reader or scanner or an RFID reader. The assembly of the input/touch screen 302 and video display 308 may be one of the aforementioned structures to which the controller 300 is coupled from which the controller 300 receives information and to which the controller 300 provides commands. According to still other embodiments, the input 302 may be in the form of computer equipment that permits the cell processing system including the controller 300 to communicate (whether via wires, cables, etc. or wirelessly) with other cell processing systems over a local network, or with other cell processing systems or other computer equipment (e.g., a server) over local networks, wide area networks, or the Internet. According to such an embodiment, the input may include an internal transmitter/receiver device.

Having discussed the structure of embodiments of the cell processing system disclosed herein, the operation of the cell processing system is now discussed. In this regard, reference is made to U.S. Patent Application Pub. No. US 2013/0092630, the contents of which are incorporated herein by reference, which document discloses methods and systems for washing biological cells using a reusable hardware apparatus and disposable fluid circuit including a spinning membrane separator which may be generally applicable to the cell processing system described herein. The methods disclosed in this document involve the processing of biological cells, such as mononuclear cells for subsequent therapeutic administration.

In general terms, the operator may first activate (e.g., switch on) apparatus 200, at which point the apparatus 200 conducts self-calibration checks, including the checking of the peristaltic pumps 202, 204, 206, clamps 210, 212, 214, 216, 218, 220, 222, and sensors 226, 238. Apparatus 200 may then prompt the user to enter or modify process parameters using the input 302, including by way of example and not by way of limitation the amount of cell suspension to be processed, the number of cycles to take place, etc. The apparatus 200 may then prompt the operator to mount the disposable set 100, after which apparatus 200 automatically checks to determine whether the disposable set 100 is properly installed. Once the set 100 is properly installed, the controller 300 prompts the operator to connect the biological fluid (e.g., 102 of FIG. 3) via a spike connector or sterile connection (e.g., 103, 104 of FIG. 3) and the wash medium (e.g., 135a, 135b of FIG. 3) via a spike connector (e.g., 134a, 134b of FIG. 3). In one embodiment, the biological fluid/cells may be apheresis-collected mononuclear cells, and the wash medium may be a saline solution.

Once the operator confirms that the solutions are connected, the controller 300 primes the disposable set 100. In the embodiment discussed above, the set 100 may be primed with saline, although other biocompatible aqueous solutions may also be used. The controller 300 then commences processing the biological fluid/cells. The biological fluid/cells is/are transferred from source container (e.g., 102 of FIG. 3) through the set to the spinning membrane separator 101 via the operation of one or more peristaltic pumps 202, 204 and 206. In a similar fashion, the wash medium is delivered from its container (e.g., 135a, 135b of FIG. 3) through the set to the spinning membrane separator 101. The biological cells are collected in either an in-process bag (e.g., 122 of FIG. 3) for additional processing or in a product container (e.g., 150 of FIG. 3), while supernatant is separated and removed to waste container (e.g., 140 of FIG. 3). Once the processing is completed, the controller prompts the operator to sample, seal and remove the product container 150.

A specific embodiment of a method 400 of operating the apparatus 200 is provided in FIG. 6. According to this embodiment, the method 400 of operating the apparatus 200 includes several steps, which steps may be grouped or organized into one or more cycles. For example, reduction, rinse and dilution steps 404, 406, 408 may define a first cycle, reduction, rinse, and dilution steps 414, 415, 416, 418 may define an optional intermediate cycle (which cycle may be omitted, or the steps 414, 415, 416 and/or 418 may be repeated several times to define intermediate cycles—e.g., a 6-cycle procedure may involve the performance of some or all of steps 414-418 a total of 4 times), and reduction, rinse, and dilution steps 424, 426, 428 may define a final cycle. It will be recognized that an apparatus 200 need not perform every step illustrated in FIG. 6, but an apparatus 200 may operate as illustrated in FIG. 6 according to this disclosure.

Preliminary to the first cycle, the controller 300 may perform an evaluation of the process to be performed by the apparatus 200 at block 390. According to certain embodiments, the evaluation is conducted using a mathematical model of the processor, as explained in detail below. The inputs for the model may include the process, or procedure, parameters received from the operator, via the input 302, for example. In the alternative or in addition, the inputs for the model may include process parameters that are stored by the controller 300, for example in the memory 306. These stored inputs may be in the form of default inputs that are used unless inputs are received via the input 302.

According to some embodiments, the mathematical model may include equations representative of the fluid flows from and to the containers 102, 122, 140, 150, of the other fluid flows within the processor 100, 200, and of the operation of the separator 101. In fact, according to preferred embodiments, the mathematical model is representative of the operation of the processor 100, 200 as illustrated in FIG. 6, from a priming step at block 402 to a final dilution step at block 428. The model may also include steps not illustrated in FIG. 6, such as an incubation step post the final dilution step at block 428. According to such embodiments, the controller 300 evaluates the entire process, from priming to final dilution, before the method 400 continues to block 402.

The results of the preliminary process evaluation at block 390 may be provided, displayed or used by the controller in different ways. For example, the controller 300 may provide or display outputs calculated as a consequence of the evaluation of the entire mathematical model, or only portions thereof, to the operator at block 392. Such outputs may include the duration of the process (as a whole), the duration of the priming step, the final volume in the waste container, the final volume in the product container, and the volume required in the wash media containers. The outputs may be provided or displayed on the display unit 308, for example. In addition or in the alternative, the controller 300 may limit or prevent the operation of the processor 100, 200 according to the process at block 394 if, for example, the process would cause the processor 100, 200 to exceed the abilities or performance characteristics of the processor 100, 200. The controller 300 may require at block 394 that an operator or an administrator (i.e., a user with greater control privileges than an operator) provide an override code (e.g., via the input 302) to allow the process to be performed. As an additional or alternative possibility, the controller 300 may limit or prevent operation of the processor 100, 200 at any point during the method 400 (e.g., at block 404) if measured in-process conditions differ from those calculated during the evaluation of the process. The measurements may involve signals received by the controller 300 from one or more of the scales 240, 242, 244, 246 mentioned above. The interruption of the process may be overridden by an operator or administrator using an override code (e.g., received by the controller 300 via the input 302) as mentioned above relative to the action at block 394.

Following this pre-process evaluation, the controller 300 may cause the apparatus 200 to perform the step of priming the set 100 at block 402. According to this step, wash media from the wash media containers 135a, 135b is transferred to the disposable set 100. Wash media may also be transferred to the source container 102. In fact, a small amount of wash media may be transferred to each of the other containers 102, 122, 140, 150 to ensure that the containers are connected 102, 122, 140, 150. To this end, the controller 300 may cause clamps 214, 216, 218, 220, 222 to open to permit the transfer of fluid to the containers 102, 122, 140, 150.

Once the priming is complete at block 402, the method 400 continues to block 404, where the controller 300 causes the apparatus 200 to perform the first cycle reduction step. According to this step, the controller 300 causes the biological fluid from the source container 102 and wash media from the wash media container(s) 135a, 135b to be transferred to the separator 101. For example, the controller 300 may open clamps 214, 212 (and/or 210) and operate pumps 204, 202 to transfer the fluids from the containers 102, 135a (and/or 135b) to the separator 101. The separator 101 (in conjunction with operation of the drive 248 by controller 300) produces two streams: a first, or retentate, stream that is directed into the in-process container 122, and a second, or filtrate, stream that is directed into the waste container 140. For example, the controller 300 may open clamp 218 and operate pump 206 to cause flow into the in-process container 122 (clamp 220 being closed), and may open clamp 222 to permit flow into the container 140. After the step of block 404 is complete, the controller 300 causes wash media to be passed through the set (i.e., the set is rinsed) and the media is added to the in-process bag 122 at block 406. This may be achieved, for example, by closing clamps 214, 222, while leaving clamps 212 (and/or 210), 218 open and operating pumps 202, 206. After block 406, the method 400 proceeds to block 408, where the controller 300 causes additional wash media to be added to the in-process bag 122. When block 408 is complete, the method 400 passes from the first cycle to the intermediate cycle.

At optional block 414, the controller 300 may cause the apparatus 200 to reduce the fluid in the in-process bag 122 further by transferring the fluid to the separator 101 without additional dilution, and passing the supernatant to the waste container 140 while the cells are returned to the in-process bag 122. For example, the controller 300 opens clamps 216, 218, 222 and operates pumps 204, 206 and drive 248. The controller 300 may continue to cause the apparatus 200 to perform this step until certain user-defined limits have been satisfied. It is also possible that the controller 300 may skip this optional step entirely while operating according to the method 400, and proceed instead to step 415.

At optional block 415, the controller 300 may cause the apparatus 200 to operate such that the feed into the separator 101 is maintained at a constant packed cell volume (PCV). Because cells are being processed from the in-process container 122, concentrated, and then directed back to the in-process container 122, the PCV of the in-process container 122 would continuously increase. To limit or prevent the continuous increase, the controller 300 causes the apparatus 200 is add wash media at increasing rates. As such, the controller may open clamp 212 (and/or 210) and clamps 216, 218, 222 while operating pumps 202, 204, 206 and drive 248, for example.

Once block 415 is complete, the controller 300 may cause the apparatus to perform a rinse of the set at block 416 and to add wash media to the in-process bag 122 at block 418. When block 418 is complete, the method 400 passes from the intermediate cycle to the final cycle.

The final cycle begins with block 424, where the controller 300 causes the biological fluid from the in-process container 122 and wash media from the wash media containers 135a, 135b to be transferred to the separator 101. For example, the controller 300 may open clamps 216, 212 (and/or 210) and operate pumps 204, 202 to transfer the fluids from the containers 102, 135a (and/or 135b) to the separator 101. Again, the separator 101 produces two streams: a first, or retentate, stream that is directed into the retentate, or product, container 150 (instead of the in-process container 122), and a second, or filtrate, stream that is directed into the waste container 140. For example, the controller 300 may open clamp 220 and operate pump 206 to cause flow into the product container 150, and may open clamp 222 to permit flow into the container 140. After the step of block 424 is complete, the controller 300 causes wash media to be passed through the set (i.e., the set is rinsed) and the media is added to the product bag 150 at block 426. This may be achieved, for example, by closing clamps 216, 222, while leaving clamps 212 (and/or 210), 220 open and operating pumps 202, 206. After the block 426, the method 400 proceeds to block 428, where the controller 300 causes wash media to be added to the product bag 150. When block 428 is complete, the method 400 may continue with other steps, such as incubation, as are desired before the product bag 150 is sampled, sealed and removed from the apparatus 200.

Figure 7:
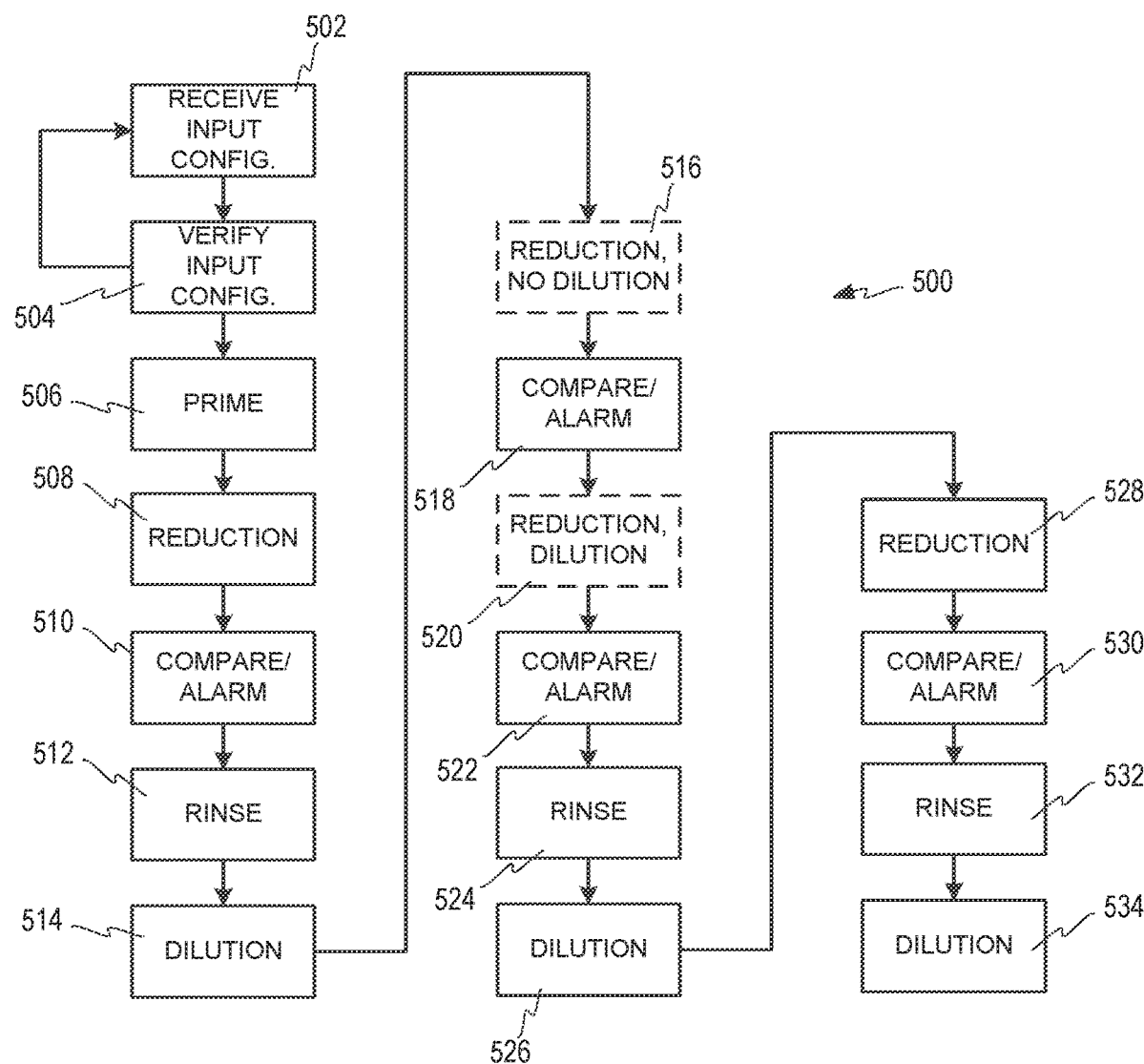
FIG. 7 is a flowchart of one embodiment of a method for evaluating a procedure, or a portion thereof, to be performed on, for example, a reusable cell processing apparatus with a disposable fluid circuit prior to the procedure being performed using the apparatus and fluid circuit.

Having discussed the method 400, a method 500 of performing the preliminary or pre-process evaluation of the process (i.e., 390 in FIG. 6) is illustrated in FIG. 7. The method 500 begins at block 502, with receipt by the controller 300 of the input configuration, i.e., the process parameters required for the processor 100, 200 to perform the process or procedure. The controller 300 may receive the input configuration via the input 302, as mentioned above. As also mentioned above, the controller 300 may receive the process parameters from the memory 306 associated with the controller 300. In fact, certain process parameters may be initialized to a default value according to values stored in the memory 306, some or all of which may be modified by the user (e.g., operator or administrator) via the input 302, for example.

The method 500 may continue at block 504, where the input configuration received at block 502 is evaluated for completeness. For example, the controller 300 may verify that a value has been received for each process parameter in the input configuration. Further, the controller 300 may verify that the values received fall within a preset range for such parameters. The controller 300 may perform other verifications as well. If the controller 300 determines that one or more of the process parameters are missing from the input configuration (or fail to fall within the required range, for example), the process 500 returns to block 502. Otherwise, the method 500 continues to block 506.

At block 506, the controller 300 performs calculations representative of the priming of the set 100 (see, block 402 of FIG. 6). For example, information regarding the number of priming actions and the identity of the source of the priming fluid (and whether that source is also used as the source for the wash media for the entire procedure) may be received. Based on this information in combination with information relating to the volume of the tubing, of the separator, etc., the controller 300 may calculate the volumes and volume fractions expected to be present in the containers at the end of the priming step, as well as the time required to perform this part or portion of the procedure. The method then continues to block 508.

At block 508, the controller 300 performs the calculations representative of the separation of the biological fluid into two streams. This is representative of the separation occurring at block 404 of FIG. 6, for example. As part of the calculations, the controller sets flow rates for each of a plurality of volumes (each volume representing one of the containers and the separator). The controller 300 also sets the initial volumes for certain of the containers and initial volume fractions. Based on this information, the controller 300 then calculates the volumes and volume fractions expected to be present in the containers at the end of the separation step, as well as other information, such as the time required to complete this part of the process and/or the time required to complete the process to this point.

In doing so, the controller 300 at block 508 uses the final volumes and final volume fractions from the preceding step as the initial volumes and initial volume fractions for this step. According to certain embodiments, including the illustrated embodiment, the controller 300 generally uses the final volumes and final volume fractions from the preceding step as the initial volumes and initial volume fractions for the following step. As a consequence, to calculate the outputs discussed above, the controller 300 first carries out the calculations for every step of the process or procedure, because each succeeding step builds on each prior step.

A comparison may be performed between certain calculated in-process conditions and controls for those conditions at block 510. While the comparison is illustrated as a separate block 510, the comparisons may be made while the calculations that occur as part of block 508 are performed. The comparison may involve determining if the calculated condition matches a control. In this regard, "matching" may include being identical to the control value, or within a certain range of control values. "Matching" may also include satisfying a particular relationship to the control value, such as exceeding or not exceeding the control value. If the comparison is not satisfied (i.e., the calculated value does not match the control value), then a warning or error indication may be provided to the operator, via the video display 308, for example.

At blocks 512, 514, the controller 300 performs calculations representative of the rinse and dilution actions performed, for example, at blocks 406, 408 in FIG. 6. As part of this calculation, the controller 300 receives information as to which wash media volume/container (e.g., container 135a or 135b) will provide the wash media for the rinse and/or dilution steps. The controller 300 uses the volumes and volume fractions from the previous step as the initial values, and then calculates the final volumes and volume fractions. The controller 300 may also calculate the procedure time for this part (or step) and/or to the completion of the step.

The method 500 continues at block 516, 520, where calculations are performed representative of the actions performed at blocks 414, 415 in FIG. 6. At block 520, because the wash media will be added at increasing rates during the corresponding step of the process 400, the controller 300 approaches the calculation of the rates, volumes and volume fractions as a series of calculations performed over an iterative timescale. Alternatively, if either corresponding step of the process (i.e., 414, 415) is omitted, then the final volumes and volume fractions at blocks 516, 520 are set equal to the initial volumes and volume fractions, and the time for the step is set equal to zero.

As was the case relative to the calculations performed at block 508, the method 500 includes comparisons of some of the calculated conditions with controls for those conditions at blocks 518, 522 (similar to block 510, above). As was also the case above, while the comparisons are illustrated as separate blocks 518, 522, the comparisons may occur during the calculations at blocks 516, 520. The method then continues at blocks 524, 526 with calculations representative of the rinse and dilution steps at blocks 416, 418 in FIG. 6. The calculations performed here are similar to those performed at blocks 512, 514.

In the same manner that the foregoing calculations and comparisons at blocks 516, 518, 520, 522, 524, 526 may be omitted if some or all of the steps of the intermediate cycle (i.e., blocks 414, 415, 416, 418) are omitted, the calculations and comparisons at blocks 516, 518, 520, 522, 524, 526 may be repeated if some or all of the steps of the intermediate cycle are repeated to define a process of more than three cycles.

The method 500 concludes with calculations at blocks 528, 532, 534 representative of the actions at blocks 424, 426, 418 in FIG. 6. The method also performs a comparison of calculated conditions and controls at block 530, similar to the comparison described above at block 510. The calculations performed at blocks 528, 532, 534 and the comparisons performed at block 530 are similar to those described above relative to blocks 508, 512, 514 and 510, and as such will not be repeated. The method 500 then concludes, with the subsequent use of the outputs and/or in-process conditions at blocks 392, 394 of FIG. 6 as discussed above.

The systems and methods described herein may be effective, for example, in the washing of cells such as red blood cells and/or white blood cells. In one example of red cell washing, stored red blood cells may be washed to remove accumulated free hemoglobin, spent storage solution, or extracellular components. The washing solution may be sterile docked or otherwise included in the closed system of the disposable processing set of the type described above. The treated cells may then be washed with the washing solution such as saline, Adsol or E-Sol (the latter of which are red blood cell storage solutions and generally comprise dextrose, mannitol and a buffer) to reconstitute the red blood cells for subsequent storage and transfusion.

The initial cell feed may be diluted by combining the feed from container 102 with diluent (wash solution) from container 135 at branched connector 126. In one embodiment, diluent from container 135 may initially be drawn into separator, followed by the cell feed drawn from container 102 and combined with the diluent, as described.

Having thus described the structure and operation of embodiments of a cell processing system that may be used with the filling options discussed herein, the filing options are discussed in detail.

Figure 8:
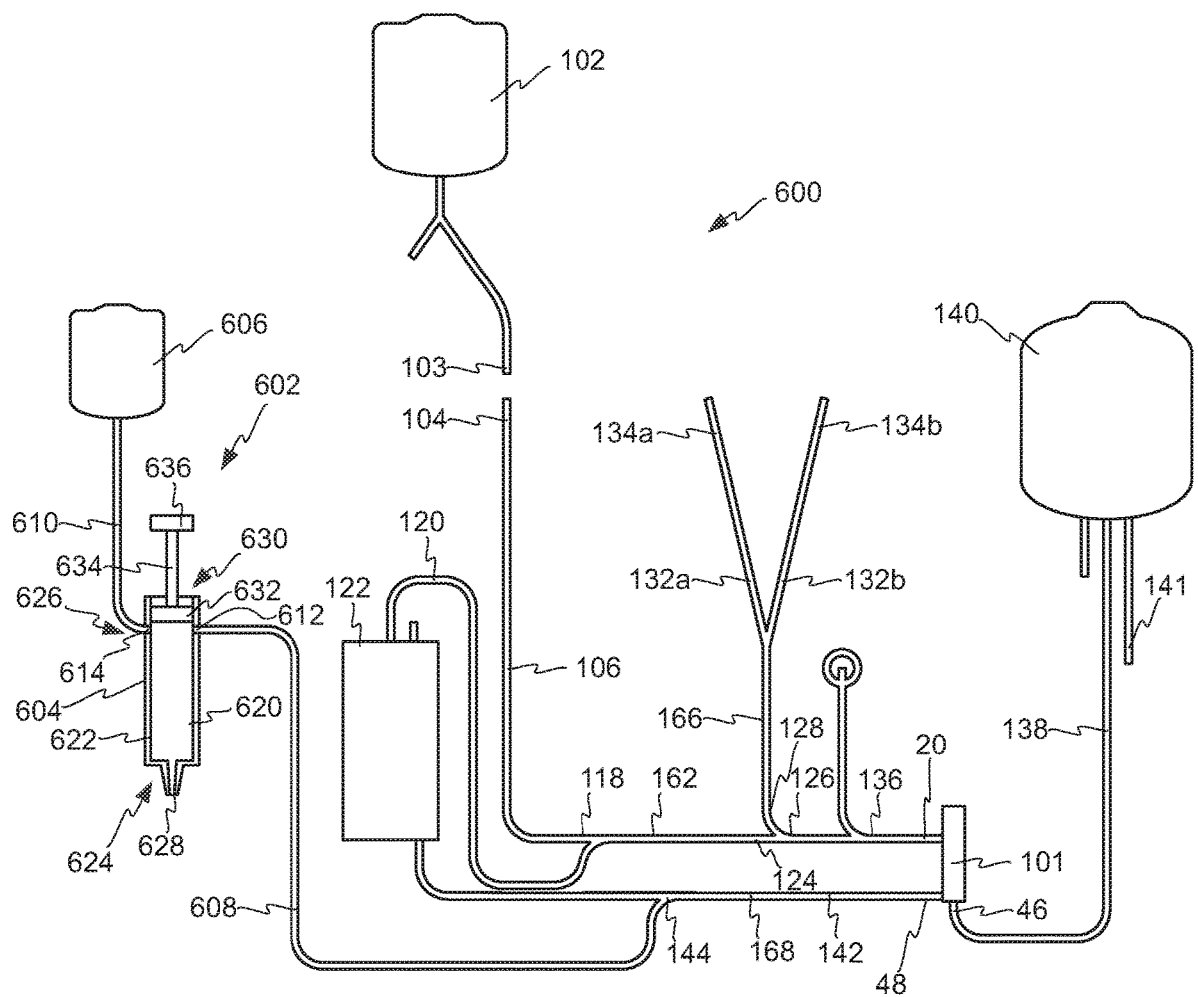
FIG. 8 is a schematic view of another embodiment of a disposable fluid circuit useful in the systems and methods described herein.
Figure 9:
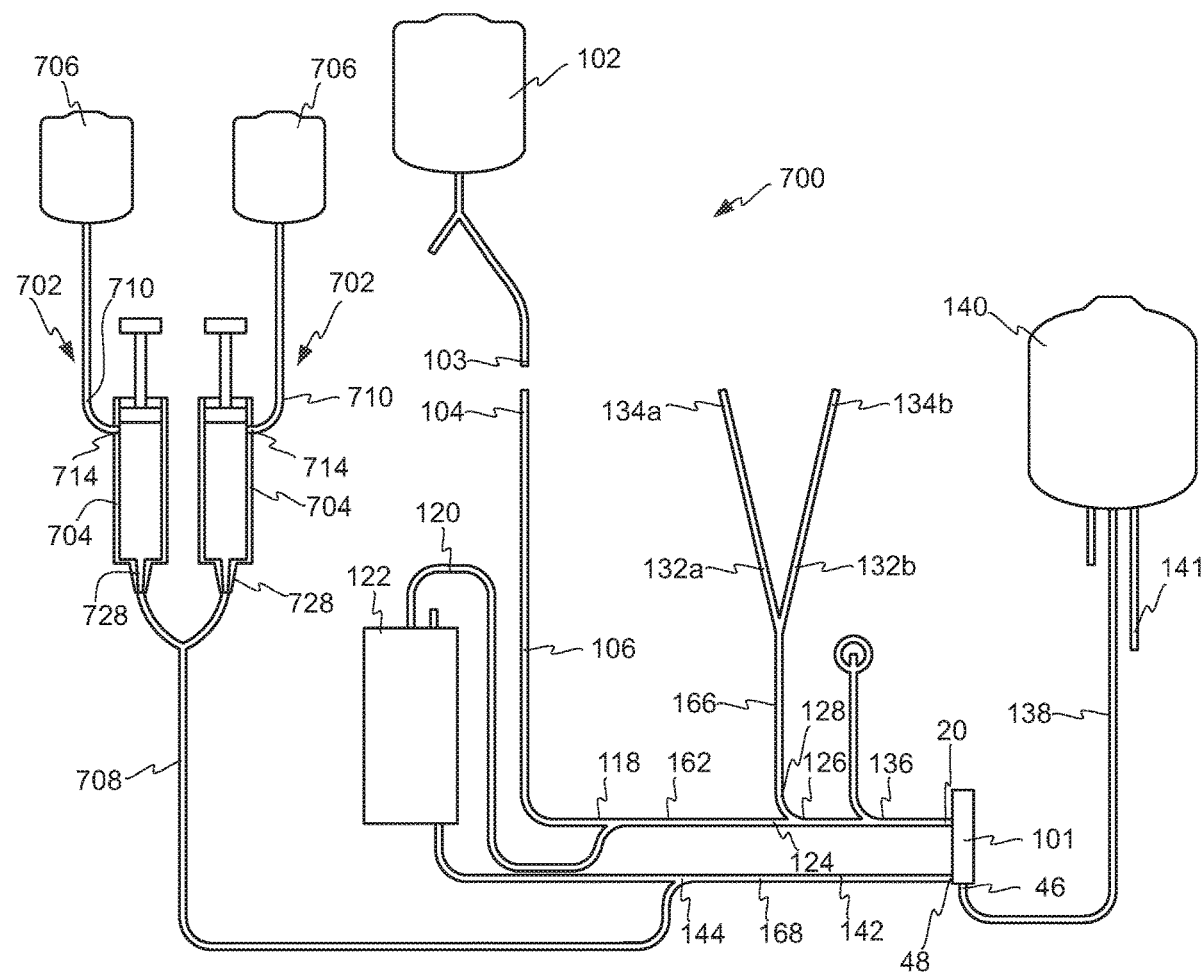
FIG. 9 is a schematic view of a still further embodiment of a disposable fluid circuit useful in the systems and methods described herein.

A first set of fill options are illustrated in FIGS. 8 and 9. These filling options make use of a substantial part of the disposable fluid circuit 100 described above, as well as the reusable hardware 200. In fact, the a common numbering scheme has been used for those structures of the circuits illustrated in FIGS. 8 and 9 that are the same or substantially the structures of the circuit 100 illustrated in FIGS. 1 and 3, and as such not every feature numbered in FIGS. 8 and 9 is re-explained relative to FIGS. 8 and 9. Some of the structures of the circuit 100 may have been omitted in the circuits of FIGS. 8 and 9 to simplify the drawings. Such omissions are not necessarily indicative of absence of such elements, except as may be explicitly delineated below.

Most significantly, the product container 150 discussed above is not included in the circuits of FIGS. 8 and 9. Instead, the filling options illustrated in FIGS. 8 and 9 substitute one or more syringes (or syringe assemblies) for the flexible-walled bag included in the previous embodiments, such as are illustrated in FIGS. 1 and 3. These syringes may be provided directly to the end-user (once certain portions of the assemblies have been separated and removed), and thus may be referred to as end-user containers, or pre-filled syringes, herein.

With reference first to FIG. 8, a circuit 600 is illustrated therein. The circuit 600 includes a spinning membrane 101, at least one container 102, 122, 140 (of which at least container 102 may be initially separate and then connected at 103, 104 to the remainder of the circuit 600 at the time of processing), and tubing 106, 120, 128, 132a, 132b, 162, 166, 168 connecting the spinning membrane 101 and the one or more containers 102, 122, 140. The tubings 132a, 132b preferably include and terminate in an access site 134a, 134b, such as spike connectors, to establish flow communication with containers 135a, 135b (shown in FIG. 1) of a wash fluid, such as saline or other solution. Tubings 132a, 132b may include in-line sterile barrier filters (such as 0.2 μm filters) for filtering any particulate from the wash fluid.

The circuit 600 includes a syringe assembly 602 instead of the product container 150 discussed above. The size of the syringe assembly 602 as illustrated in FIG. 8 is not to scale with the remainder of the circuit 600. Instead, the assembly 602 has been enlarged to permit better visualization of the details of the assembly 602 and to facilitate its description.

The syringe assembly 602 includes a syringe 604 and an auxiliary container, or vent bag, 606, and may be in the form of a flexible-walled bag. The syringe 604 is connected to and in fluid communication with the remainder of the circuit 600 via tubing 608, and the syringe 604 is connected to and in fluid communication with the vent bag 606 via tubing 610. In particular, the tubing 608 connects to the syringe 604 at a port 612, and the tubing 610 connects to the syringe 604 at a port 614.

The syringe 604 may include a cylinder or barrel 620 defined by a wall 622 through which the tubing 608, 610 is connected at ports 612, 614. The ports 612, 614 may be openings or orifices through the wall 622 according to one embodiment. The barrel 620 has a first end 624 and a second end 626 disposed at opposite ends of the barrel 620. The first end 624 may include a luer tip 628, for example, through which the contents of the syringe 604 may be ejected, and which may be connected to a mating luer connector or a needle tip at the time of use. A plunger assembly 630 is disposed through the second end 626 of the barrel 620, and as illustrated includes a plunger 632, a plunger rod or arm 634, and a thumb rest 636. A plunger assembly 630 as illustrated may be used by a healthcare professional to administer the contents of the syringe 604 manually; the plunger assembly 632 may include only the plunger 632 or the plunger 632/plunger rod 634 in embodiments where the syringe 604 is intended for automated administration in combination with a pump or on-body injector.

The syringe 604 may include structures other than those illustrated. For example, the syringe 604 may include finger grips that may be used in conjunction with the thumb rest 636 to apply force to the plunger assembly 630 to move the plunger 632 from one end 626 to the other 624. The syringe 604 may also include variations to the structures illustrated. For example, instead of a luer tip at the end 624, the barrel 620 may terminate in a detachable solid cap or pierceable septum that completely closes the barrel 620 at end 624, which cap may be replaced with or which septum may be pierced by an administration assembly (e.g., needle and hub) at the time of use.

The syringe assembly 602 also may include additional structures. For example, a clamp may be disposed on the tubing 610 between the syringe 604 and the vent bag 606. The syringe assembly 602 may also include a hanger for attaching the syringe to scale 240 so that the controller 300 may use the scale 240 to determine the weight, and thus the amount, of fluid that has been directed into the barrel 620 of the syringe 604.

In operation, the syringe assembly 602 would be used much in the same way the container 150 is used, as explained above. The product is received by the syringe assembly 602 from the spinning membrane 101 during the final cycle of the process. In particular, the plunger assembly 630 is retracted or withdrawn from the barrel 620 to such an extent that the plunger 632 is disposed adjacent the end 626, preferably preventing the plunger 632 from interfering with the passage of fluid from the remainder of the circuit 600 into the barrel 620 via the port 612 and the passage of gas (e.g., air) out of the barrel 620 into the vent bag 606 via the port 614. According to certain embodiments and certain operational conditions, the plunger 632 may partially occlude the ports 612, 614. The plunger 632 may be maintained in this condition by placing a stopper or spacer between the thumb rest 636 and the edge of the wall 622 of the barrel 620 of the syringe 604. If a clamp has been placed on the tubing 610, it would be opened when the syringe 604 is being filled.

As product enters the syringe 604 (and in particular the barrel 620), the gas that had been present in the barrel 620 passes into the vent bag 606. Consequently, it is desirable to have the volume of the vent bag 606 be greater than or at least equal to the volume of the syringe 604 in the barrel 620 with the plunger 632 disposed as described in the previous paragraph (which may be referred to herein as the "retracted position"). In fact, considering that the volume of the syringe 604 may be on the order of a few mL (e.g., 25 mL), it may be highly desirable to use the pre-processing evaluation described above when using this fill option to ensure that the volume of product transferred to the syringe 604 does not exceed the volume of the syringe 604.

Variations of the syringe assembly 602 illustrated in FIG. 8 are possible. For example, FIG. 9 illustrates an embodiment of a circuit 700 wherein two syringe assemblies 702 are connected to the remainder of the circuit 700. Each of the syringe assemblies 702 includes a syringe 704 and a vent bag 706. While the syringes 704 are connected to their respective vent bags 706 via tubing 710 at ports 714, the reminder of the circuit 700 is connected to the syringes 704 via tubing 708 and a Y-connector at the luer tips 728 of each of the syringes 704. In fact, in is possible in the embodiment illustrated in FIG. 8 for the tubing 608 to be connected to the syringe 604 via the luer tip 628 instead of via the port 612 in the wall 622 of the barrel 620. Otherwise, the structure and operation of the syringe assemblies 702 and the circuit 700 may be substantially as described above, with the associated clamps opened for each of the syringe assemblies 702 prior to filling and then closed once the syringe 704 had been filled as desired.

While an embodiment of a circuit 700 with two syringe assemblies 702 is illustrated in FIG. 9, other embodiments could include a larger number of syringe assemblies (e.g., three or more).

A second set of fill options are illustrated in FIGS. 10-14. According to these embodiments, the processor 200 is used with or as a filling system to distribute the product from the circuit 100 and/or a product container 150 into a plurality of other containers, for storage, shipment or both after processing of the biological fluid. In fact, it may be possible to fill a plurality of containers from one or more product containers 150 using such an embodiment, where the volume of the individual containers being filled are smaller, even many times smaller, than the volume of the product container(s) 150. According to certain embodiments, the volume of the individual containers to be filled may be at least an order of magnitude smaller than the volume of the product container 150.

To this end, the product container 150 may be connected to a new circuit, which circuit is either used with a separate pump or one or the pumps of the processor 200 to distribute the product from product container 150 to one or more additional containers. The processor 200 (and in particular, the controller 300) may be in communication with the filling system, and data may be transmitted back and forth between the processor 200 and the filling system or may be shared between the processor 200 and the filing system. In fact, the filling system may have its own controller (which controller may include a microprocessor, other circuits or circuitry and one or more memories, which may be one or more tangible non-transitory computer readable memories, with computer executable instructions by which the microprocessor is programmed and which when executed by the microprocessor may cause the microprocessor to carry out one or more actions being stored on the memory/memories) that is in communication with the controller 300.

Figure 10:
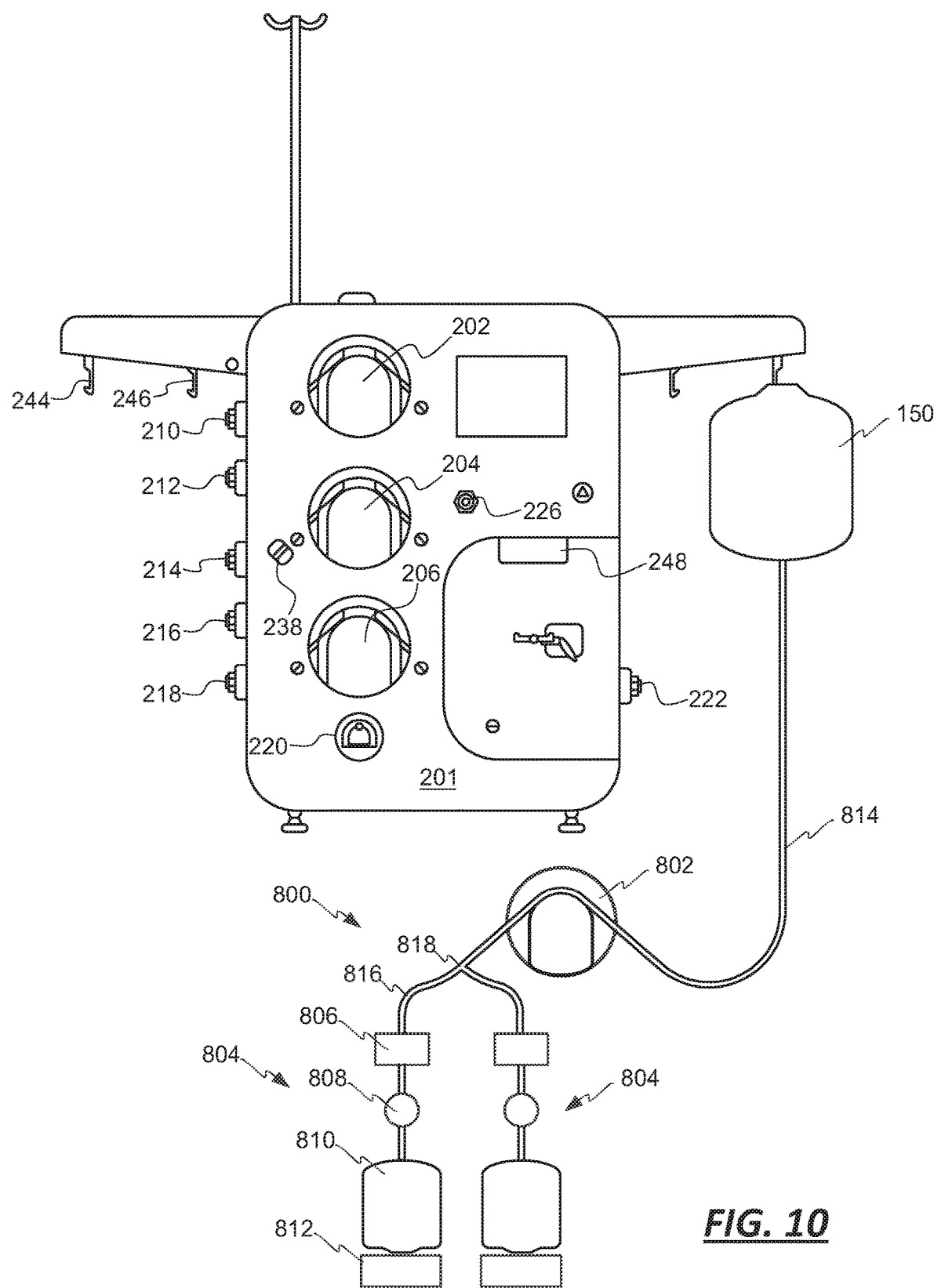
FIG. 10 is a frontal view of a reusable cell processing apparatus with a product container loaded thereon in combination with a filling system.

First with reference to FIG. 10, an embodiment including a separate filling system 800 is illustrated. The filling system 800 may include a pump 802 (which may be in the form of a peristaltic pump) and one or more filling stations 804. Each of the filling stations 804 may include a sensor 806 (e.g., an air detector, a hematocrit detector, or another detector configured to determine, for example, the concentration of a cell of interest—further exemplary detectors are described in U.S. Pat. No. 8,556,793 and U.S. Publ. No. 2015/0122997, which patents and publications are incorporated by reference in their entirety herein), a mechanism for controlling fluid flow (e.g., a clamp or valve) 808, a container 810 (such as a flexible walled bag), and a scale 812 to determine the weight (and thus the amount) of product in the container 810. While the scale 812 is illustrated as beneath each of the containers 810, it will be recognized that the container 810 may be hung from the scale 812 instead as in FIG. 1.

Each of the filling stations 804 is connected to the product container 150 by tubing 814, 816 and a Y-connector 818. The tubing 814 is connected at a first end to the product container 150 (e.g., via a port of the product container 150) and at a second end to the Y-connector 818, while the region intermediate to the first and second ends is disposed in the pump 802. Additional tubing may connect the sensor 806, clamp 808 and container 810.

The filling stations 804 may include additional equipment as well. For example, each filing station may include a substation for forming a sterile connection between the tubing of the filling station 804 and the container 810. Such a sterile connection substation may include a mechanism that connects the ends of the tubing of the filling station 804 and the container 810 without exposing the interior of the tubing to ambient contamination. The filling system 800 may include a single sterile connection substation for all of the associated filling stations 804, or each filling station 804 may include its own sterile connection substation.

Figure 11:
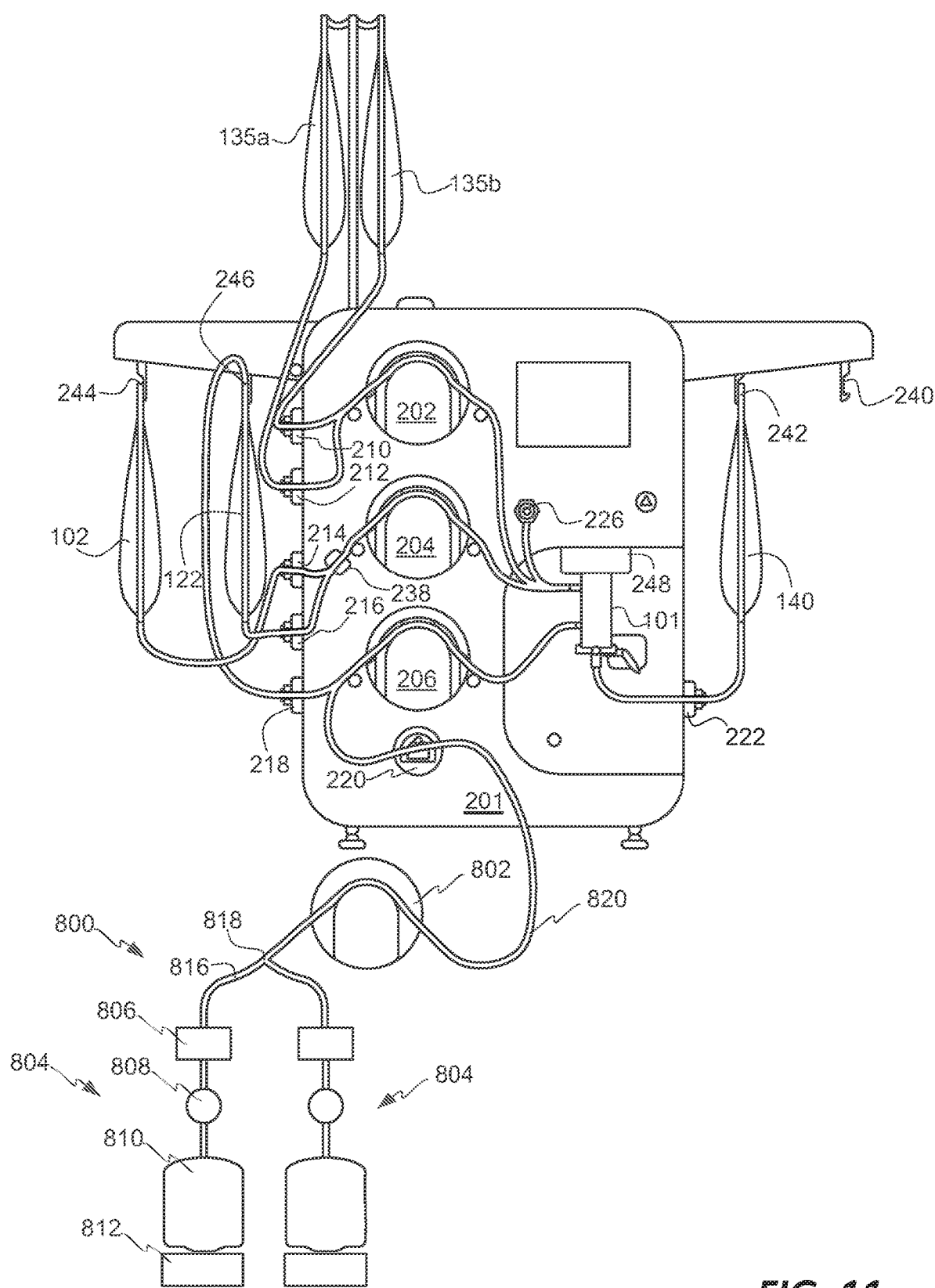
FIG. 11 is a frontal view of a reusable cell processing apparatus with another disposable fluid circuit loaded thereon in combination with filling system.

A further variant of this embodiment is illustrated in FIG. 11. The embodiment of FIG. 11 is similar to that of FIG. 10, and like elements are numbered in like fashion. Unlike the embodiment of FIG. 10, the embodiment of FIG. 11 includes tubing 820 that is connected to the separator 101. That is, rather than connecting the filling system 800 to the remainder of the circuit 100 via the product container 150 (which connection may only be an indirect one, as the product container 150 may be separated and no longer in fluid communication with the circuit 100 when the filling station 800 is attached to the product container 150), the filling station may 800 may be directed connected and in selective fluid communication with the circuit 100, and in particular the separator 101, via the tubing 820. The clamp 220 may be use to open and close the fluid communication between the filling system 800 and the circuit 100.

Figure 12:
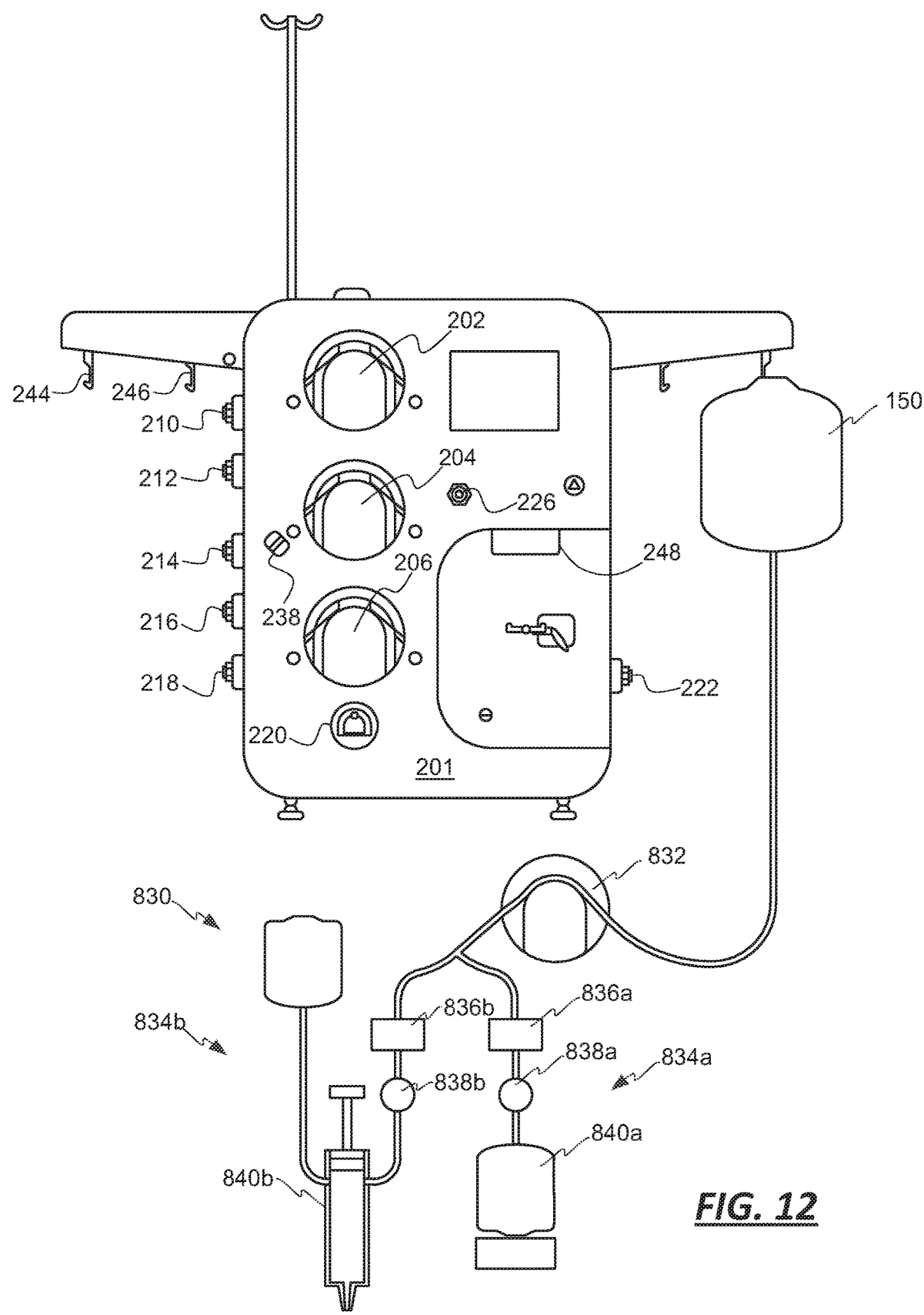
FIG. 12 is a frontal view of a reusable cell processing apparatus with a product container loaded thereon in combination with another filling system.

Additionally, it is not necessary that each of the filling stations 804 include exactly the same equipment or the same kind of container. For example, as illustrated in FIG. 12, a filling system 830 is illustrated, including a pump 832 and filling stations 834a, 834b. Each of the filling stations 834a, 834b includes a sensor 836a, 836b and a clamp 838a, 838b. However, while the filling station 834a includes a container 840a in the form of a flexible walled bag, the filling station 834b includes a syringe assembly 840b, similar to the syringe assemblies 602, 702 illustrated in FIGS. 8 and 9 discussed above. For example, the syringe assembly 840b may include a syringe, a vent bag, and tubing to connect the syringe to the clamp 838b and the vent bag. To this extent, the statements made above relative to the syringe assemblies 602, 702 may apply in equal measure to the syringe assembly 840b.

Figure 13:
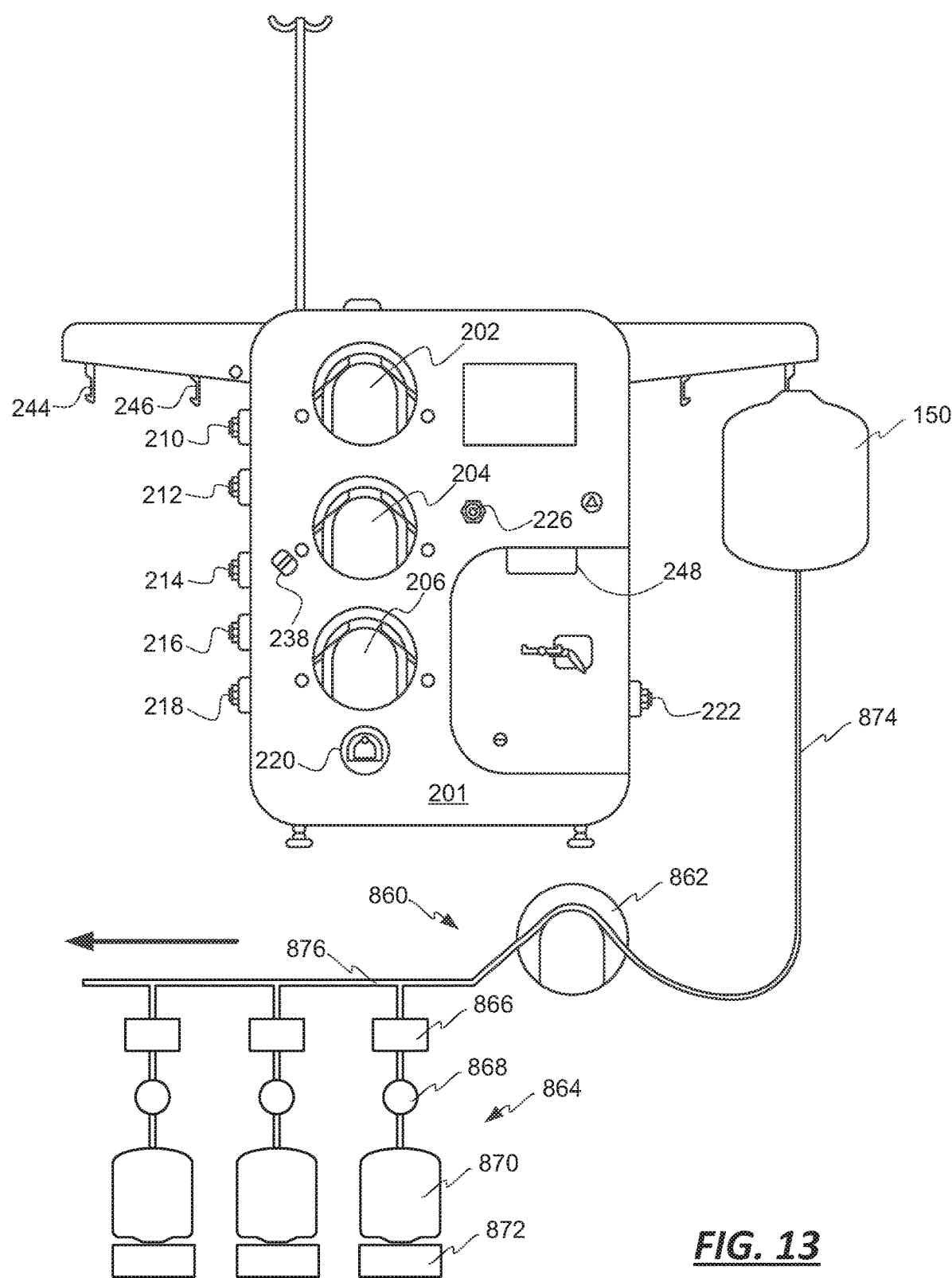
FIG. 13 is a frontal view of a reusable cell processing apparatus with a product container loaded thereon in combination with yet another filling system.

According to still further embodiments of the filling system, the filling stations may be connected to a single manifold, the manifold being connected to the product container 150. FIG. 13 illustrates such a filling system 860. Like the other filling systems discussed above, the system 860 includes a pump 862 and a plurality of filling stations 864. Each filling station 864 includes a sensor 866, a clamp 868, a container 870 and a scale 872. Further, each filling station is connected to tubing 874 that is connected to the product container 150 and is disposed in the pump 862.

However, unlike the embodiments illustrated in FIGS. 10-12, where each filling station is connected via a Y-connector to the tubing connected to the product container 150, each of the filling stations 864 is connected to a common manifold (or main line) 876 that is connected to the tubing 874. While three filling stations 864 are illustrated as connected to the manifold 876, additional filling stations may be connected to the manifold 876, as represented by the arrow at the left end of the manifold 876.

Figure 14:
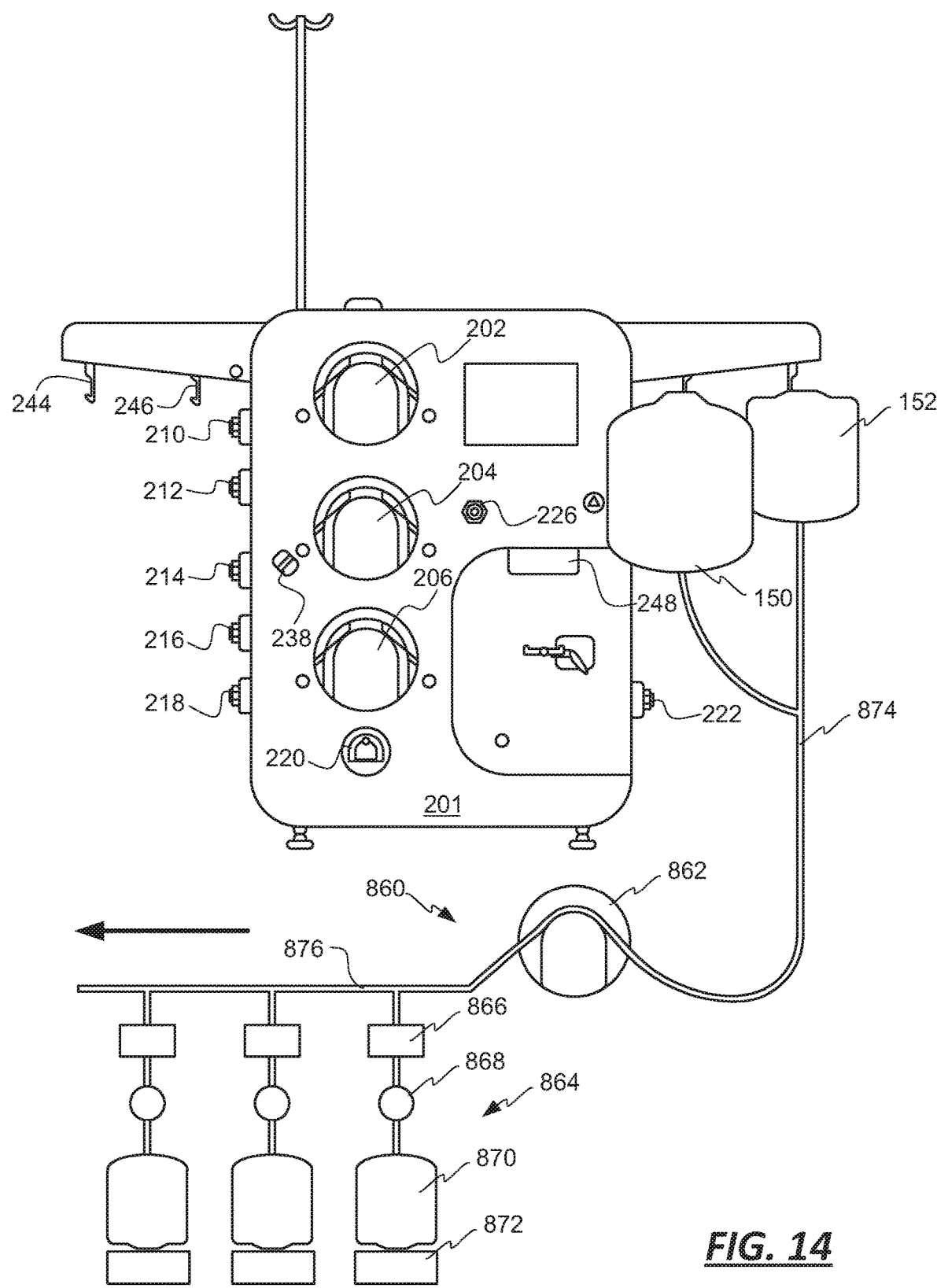
FIG. 14 is a frontal view of a reusable cell processing apparatus with a product container and an ancillary fluid container loaded thereon in combination with the filling system of FIG. 13.

A further variant of this set of embodiments is illustrated in FIG. 14. The embodiment of FIG. 14 is similar to that of FIG. 13, and like elements are numbered in like fashion. Unlike the embodiment of FIG. 13, the embodiment of FIG. 14 includes tubing 874 that is connected to the product container 150 and a fluid container 152. The containers 150, 152 may be connected to the tubing 874 via a Y-connector. According to this embodiment, each of the containers 870 at each of the filling stations 864 is filled with product from the product container 150 and fluid from the fluid container 152. The fluid transferred or drawn from the container 152 may be cryoprotectant or a media reagent, for example.

According to one embodiment of a method of operating the filling system 860 illustrated in FIG. 14, certain information (or data) is obtained regarding the characteristics of the product in the product container 150 and the desired characteristics of the contents in each of the containers 870. For example, this information may include the concentration of the product cells in the product container and the total volume of the product container 150, as wells as the desired concentration in each of the containers 870 and the volume (or capacity) for each of the containers 870. The number of containers 870 to be filled is also obtained. This information could be input manually into a controller associated with the filling system 860, or the information could be transferred or transmitted from the controller 300 associated with the processor 200 to the controller associated with the filling system 860. From this information, the desired amount of product from the product container 150 and fluid from the fluid container can be determined, as well as an evaluation performed to ensure that sufficient product and fluid is present prior to initiation of the filling process.

The method then continues with the opening of the clamp 868 associated with the first filling station 864, the clamps associated with the other filling stations 864 remaining closed at this point. The pump 862 is actuated in a particular direction (e.g., counterclockwise) for a specific duration to achieve a desired contents (or dose) in the container 870.

The sensor 866 is used to monitor the concentration of the product flowing into the container 870 to confirm that the product entering the container 870 is homogenous, within tolerances. If the sensor 866 determines that the concentration varies (outside of tolerances), an alarm may be actuated so that a remedial action may be taken (e.g., shaking or agitating the product container 150). The sensor 866 may also provide a total cell count for the product distributed into the container 870.

At the same time, the pump 862 may be monitored to determine the number of pump strokes that have occurred since the beginning of the fill process. Each pump stroke provides a certain amount of fluid per unit time (e.g., minute), and from this information the amount of product pumped can be determined. Assuming a homogenous concentration for the product, the number of cells pumped can be determined, and thus the amount of product transferred to the container 870.

The scale 872 is also monitored to determine when the desired amount of product and fluid has been transferred to the container 870. Once the desired amount of product and fluid has been transferred to the container 870, the pump 862 is stopped and the clamp 868 is closed. Before the clamp 868 associated with a different filling station 864 is opened, the pump 862 is reversed (e.g., operated clockwise) to withdraw the product and fluid in the tubing of the filling station 864 above the clamp 868 to the manifold 876. The filling system 860 is then prepared to fill another container 870 at another filling station 864.

Figure 15:
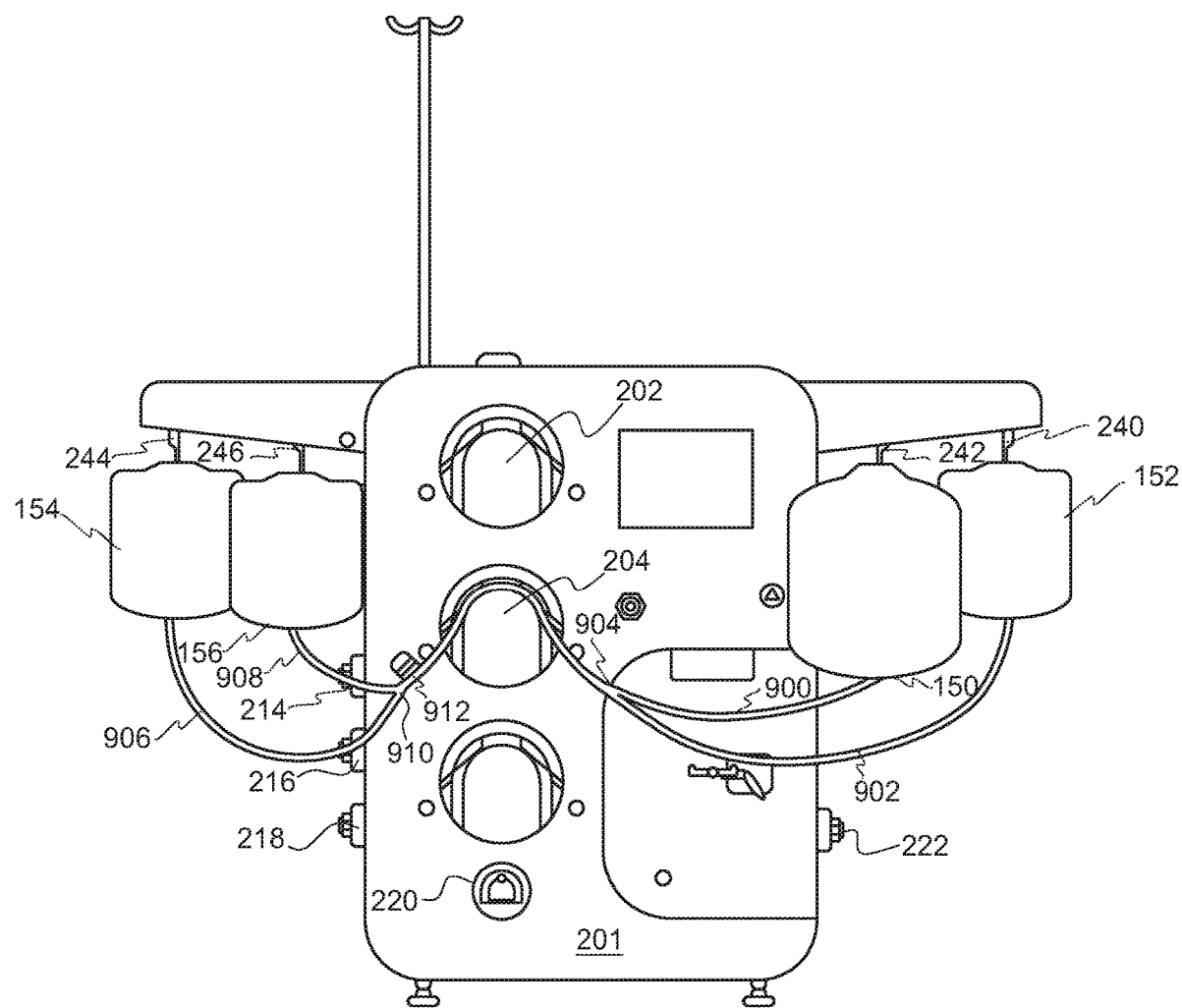
FIG. 15 is a frontal view of a reusable cell processing apparatus with another disposable fluid circuit loaded thereon, the reusable cell processing apparatus being used as a filling system.

A still further variant wherein the processor 200 may be used as the cell processing system, as explained above (with reference to FIGS. 1-7), and as the filling system is illustrated in FIG. 15. In this case, the filling system includes the pump 204 and two filling stations. Each of the filling stations includes a clamp 214, 216, a container 154, 156 and a scale 244, 246. Thus, clamp 216, container 154 and scale 244 define the first filling station, and clamp 214, container 156, and scale 246 define the second filling station.

Similar to the embodiment of FIG. 14, the embodiment of FIG. 15 includes a product container 150 and a fluid container 152, the contents of which is used to fill the containers 154, 156. Containers 150, 152 are connected to one end of tubing 900, 902, the other end of which is connected to a Y-connector 904. In a similar fashion, containers 154, 156 are connected to one end of tubing 906, 908, the other end of which is connected to a Y-connector 910. The Y-connector 904 is connected to the Y-connector 910 by tubing 912. An intermediate section of tubing 912 is disposed in pump 204, while intermediate sections of tubing 906, 908 are disposed in clamps 214, 216.

According to one embodiment of a method of operating the filling system illustrated in FIG. 15, the process beings with the attachment of the product container 150 to the tubing set as described above. The controller 300 then determines the weight of the product in the product container 150 via the scale 242. The controller 300 also determines the weight of the fluid in the container 152 via the scale 240. The controller 300 may also determine the weights of the empty containers 154, 156 via the scales 244, 246.

The controller 300 then operates clamp 214 to open the path between the container 156 and the containers 150, 152. The pump 204 is moved in a counterclockwise direction to draw fluid from the product container 150 and to draw fluid from the container 152. The controller 300 monitors the scale 246, or the number of pump strokes and the scale 246, to determine when the amount of product and fluid in the container 156 is equal to the desired volume, providing the desired concentration. At this point, the controller 300 operates the clamp 214 to close the path between the container 156 and the containers 150, 152.

The controller 300 then operates the pump 204 in a clockwise direction with clamp 214 and clamp 216 closed to transfer the contents of the path between the clamp 214 and the Y-connector 910 to the tubing 912, or even further in the direction of the Y-connector 904. Once this is achieved, the pump 204 is stopped.

The controller 300 then operates clamp 216 to open the path between the container 154 and the containers 150, 152. The pump 204 is moved in a counterclockwise direction to draw fluid from the product container 150 and to draw fluid from the container 152. The controller 300 monitors the scale 244, or the number of pump strokes and the scale 244, to determine when the amount of product and fluid in the container 154 is equal to the desired volume providing the desired concentration. At this point, the controller 300 operates the clamp 216 to close the path between the container 154 and the containers 150, 152.

As a final step, the tubing 906, 908 could be rinsed with solution or air from the tubing 900. For example, the clamps 214, 216 could be opened and closed back and forth to achieve the desired rinsing.

Thus, an improved method and system have been disclosed for the processing of biological cells and the filling of containers. The description provided above is intended for illustrative purposes only and is not intended to limit the scope of the invention to any specific method, system, or apparatus, or device described herein except as may be explicitly delineated above.

In conclusion, according to one aspect, a cell processing system includes a processor connectable to a source container filled with a biological fluid. The processor, in turn, includes a separator configured to separate the biological fluid from the source container into at least two streams, and at least one syringe assembly configured to receive one of the at least two streams. The at least one syringe assembly includes a syringe having a barrel and a plunger that defines a volume that is in fluid communication with the one of the at least two streams.

According to such a cell processing system, the at least one syringe assembly may include an auxiliary container in fluid communication with the volume to receive a gas displaced from the volume. The syringe may have a first port in fluid communication with the separator and a second port in fluid communication with the auxiliary container, the barrel being defined by a wall and the first and second ports including openings through the wall. Alternatively, the syringe may have a luer tip in fluid communication with the separator and a port in fluid communication with the auxiliary container, the barrel being defined by a wall and the port including an opening through the wall.

According to other aspects, wherein the syringe may have a plunger rod attached to the plunger, and a thumb rest attached to the plunger rod. Further, the processor may include a scale, the syringe assembly attached to the scale and the scale being configured to monitor the weight of the syringe assembly.

According to another aspect, a processing and filling system includes a cell processing system and a filling system. The cell processing system includes a processor connectable to a source container filled with a biological fluid. The processor, in turn, includes a separator configured to separate the biological fluid from the source container into at least two streams. The filling system is associated with the cell processing system and proximate to the cell processing system, and includes at least one filling station in fluid communication with the cell processing system, the filling station including at least one container in selective fluid communication with the cell processing system, and a pump configured to transfer a product from the cell processing system to the at least one filling station.

According to certain aspects, the at least one container includes a syringe assembly, the syringe assembly including a syringe having a barrel and a plunger that defines a volume that is in fluid communication with the cell processing system. In addition or in the alternative, the at least one container includes a flexible bag.

According to other aspects, the filling system includes a manifold in fluid communication with the cell processing system, each of the at least one filling stations in fluid communication with the manifold. The at least one filling station may include a clamp to selectively control the flow of fluid to the at least one container, a sensor to monitor the fluid flowing into the at least one container, and a scale configured to monitor the weight of the at least one container. The filling system may include a plurality of filling stations.

According to additional aspects, the at least one filling station is in selective fluid communication with the cell processing system and a fluid container, and the pump is configured to transfer a product from the cell processing system and a fluid from the fluid container to the at least one filling station.

According to still other aspects, the cell processing system includes a disposable circuit including the product container and reusable hardware, the circuit and the hardware defining the separator.

According to any of the foregoing, the at least one filling station is in fluid communication with the separator, or the cell processing system includes a product container configured to receive one of the at least two streams from the separator, and the at least one filling station is in fluid communication with the product container. In the latter case, the volume of the at least one container may be at least an order of magnitude smaller than the volume of the product container.

According to a further aspect, a processing and filling system includes a cell processing system and a filling system. The cell processing system includes a first disposable circuit connectable to a source container filled with a biological fluid and reusable hardware including a pump. The first disposable circuit and the reusable hardware define a separator configured to separate the biological fluid from the source container into at least two streams, and a product container configured to receive one of the at least two streams. The filling system includes a second disposable circuit connectable to the product container and the reusable hardware. The second disposable circuit and reusable hardware define at least one filling station, the filing station including at least one container in selective fluid communication with the product container, and the pump of the reusable hardware is configured to transfer a product from the product container to the at least one filling station.

According to certain aspects, the reusable hardware includes at least one clamp and at least one scale, and at least one of the at least one containers, at least one clamps, and the at least one scales define one of the at least one filling stations.

According to other aspects, the processing and filling system includes a controller, the controller being configured to operate the separator to separate the biological fluid from the source container into at least two streams and to direct one of the two streams into the product container, and to operate the pump to transfer a product from the product container to the at least one filling station.

According to further aspects, the second disposable circuit and reusable hardware define a plurality of filling stations. The at least one filing station may be in selective fluid communication with the product container and a fluid container, and the pump is configured to transfer a product from the product container and a fluid from the fluid container to the at least one filling station.

According to still further aspects, the first disposable circuit includes a spinning membrane that defines, at least in part, the separator.

Other Aspects

Aspect 1. A cell processing system comprising a processor connectable to a source container filled with a biological fluid, the processor comprising a separator configured to separate the biological fluid from the source container into at least two streams, and at least one syringe assembly configured to receive one of the at least two streams, the at least one syringe assembly comprising a syringe having a barrel and a plunger that defines a volume that is in fluid communication with the one of the at least two streams.

Aspect 2. The cell processing system according to aspect 1, wherein the at least one syringe assembly includes an auxiliary container in fluid communication with the volume to receive a gas displaced from the volume.

Aspect 3. The cell processing system according to aspect 2, wherein the syringe has a first port in fluid communication with the separator and a second port in fluid communication with the auxiliary container, the barrel being defined by a wall and the first and second ports comprising openings through the wall.

Aspect 4. The cell processing system according to aspect 2, wherein the syringe comprises a leer tip in fluid communication with the separator and a port in fluid communication with the auxiliary container, the barrel being defined by a wall and the port comprising an opening through the wall.

Aspect 5. The cell processing system according to any one of the aspects 1-4, wherein the syringe comprises a plunger rod attached to the plunger, and a thumb rest attached to the plunger rod.

Aspect 6. The cell processing system according to any one of aspects 1-5, wherein the processor comprises a scale, and the syringe assembly attached to the scale, the scale being configured to monitor the weight of the syringe assembly.

Aspect 7. A processing and filling system comprising a cell processing system comprising a processor connectable to a source container filled with a biological fluid, the processor comprising a separator configured to separate the biological fluid from the source container into at least two streams, and a filling system associated with the cell processing system and proximate to the cell processing system, the filling system comprising at least one filling station in fluid communication with the cell processing system, the filing station comprising at least one container in selective fluid communication with the cell processing system, and a pump configured to transfer a product from the cell processing system to the at least one filling station.

Aspect 8. The processing and filling station according to aspect 7, wherein the at least one container comprises a syringe assembly, the syringe assembly comprising a syringe having a barrel and a plunger that defines a volume that is in fluid communication with the cell processing system.

Aspect 9. The processing and filling station according to aspect 7 or 8, wherein the at least one container comprises a flexible bag.

Aspect 10. The processing and filling station according to any one of the aspects 7-9, wherein the filling system comprises a manifold in fluid communication with the cell processing system, each of the at least one filling stations in fluid communication with the manifold.

Aspect 11. The processing and filling station according to any one of the aspects 7-10, wherein the at least one filling station comprises a clamp to selectively control the flow of fluid to the at least one container, a sensor to monitor the fluid flowing into the at least one container, and a scale configured to monitor the weight of the at least one container.

Aspect 12. The processing and filling station according to any one of the aspects 7-11, wherein the filling station comprises a plurality of filling stations.

Aspect 13. The processing and filling system according to any one of aspects 7-12, wherein the filing station is in selective fluid communication with the cell processing system and a fluid container, and the pump is configured to transfer a product from the cell processing system and a fluid from the fluid container to the at least one filling station.

Aspect 14. The processing and filling system according to any one of aspects 7-13, wherein the cell processing system comprises a disposable circuit including the product container and reusable hardware, the circuit and the hardware defining the separator.

Aspect 15. The processing and filling system according to any one of aspects 7-14, wherein the at least one filling station is in fluid communication with the separator.

Aspect 16. The processing and filling system according to any one of aspects 7-14, wherein the cell processing system comprises a product container configured to receive one of the at least two streams from the separator, and the at least one filling station is in fluid communication with the product container.

Aspect 17. The processing and filling system according to aspect 16, wherein the volume of the at least one container is at least an order of magnitude smaller than the volume of the product container.

Aspect 18. A processing and filling system comprising a cell processing system comprising a first disposable circuit connectable to a source container filled with a biological fluid and reusable hardware comprising a pump, the first disposable circuit and the reusable hardware defining a separator configured to separate the biological fluid from the source container into at least two streams, and a product container configured to receive one of the at least two streams, and a filling system comprising a second disposable circuit connectable to the product container and the reusable hardware, the second disposable circuit and reusable hardware defining at least one filling station, the filing station comprising at least one container in selective fluid communication with the product container, and the pump of the reusable hardware configured to transfer a product from the product container to the at least one filling station.

Aspect 19. The processing and filling system according to aspect 18, wherein the reusable hardware comprises at least one clamp and at least one scale, and at least one of the at least one containers, at least one clamps, and the at least one scales define one of the at least one filling stations.

Aspect 20. The processing and filling system according to aspect 18 or 19, further comprising a controller, the controller configured to operate the separator to separate the biological fluid from the source container into at least two streams and to direct one of the two streams into the product container, and to operate the pump to transfer a product from the product container to the at least one filling station.

Aspect 21. The processing and filling system according to any one aspects 18-20, wherein the second disposable circuit and reusable hardware define a plurality of filling stations.

Aspect 22. The processing and filling system according to any one of aspects 18-21, wherein the filing station is in selective fluid communication with the product container and a fluid container, and the pump is configured to transfer a product from the product container and a fluid from the fluid container to the at least one filling station.

Aspect 23. The processing and filling system according to any one of aspects 18-22, wherein the first disposable circuit comprises a spinning membrane that defines, at least in part, the separator.

The invention claimed is:

1. A cell processing system comprising:
a processor connectable to a source container filled with a biological fluid, the processor comprising:
a separator configured to separate the biological fluid from the source container into at least two streams; and
at least one syringe assembly configured to receive one of the at least two streams, the at least one syringe assembly comprising a syringe having a barrel defined by a wall and having a first end including a tip and a port through the wall near an opposed second end, and an imperforate plunger configured to be held in a retracted stationary position with all plunger portions that seal to the barrel wall being located between the port and the second end of the barrel to define a volume between the plunger and the first end of the barrel, with the volume being in direct fluid communication with the one of the at least two streams,
wherein the at least one syringe assembly includes an auxiliary container connected to the syringe at the port and in direct fluid communication with the volume and configured to receive a gas displaced from the volume with the plunger held in the retracted stationary position when the syringe receives fluid from the one of the at least two streams.

2. The cell processing system according to claim 1, wherein the syringe has another port through the wall and which is in fluid communication with the separator.

3. The cell processing system according to claim 1, wherein the tip comprises a luer tip in fluid communication with the separator.

4. The cell processing system according to claim 1, wherein the syringe comprises a plunger rod attached to the plunger, and a thumb rest attached to the plunger rod.

5. The cell processing system according to claim 1, wherein the processor comprises a scale, and the syringe assembly is attached to the scale, the scale being configured to monitor the weight of the syringe assembly.

6. The cell processing system according to claim 1, wherein the syringe is configured as an end-user container.

7. The cell processing system according to claim 1, wherein when the plunger is in the retracted stationary position, the volume between the plunger and the first end of the barrel is unobstructed.

8. The cell processing system according to claim 1, comprising a closed disposable circuit including the separator, the syringe, and the auxiliary container.

9. A processing and filling system comprising:
a cell processing system comprising:
a processor connectable to a source container filled with a biological fluid, the processor comprising:
a separator configured to separate the biological fluid from the source container into at least two streams; and
a filling system associated with the cell processing system and proximate to the cell processing system, the filling system comprising:
at least one filling station in fluid communication with the cell processing system, the filing station comprising at least one container in selective fluid communication with the cell processing system,
wherein the at least one container comprises a syringe assembly, the syringe assembly comprising a syringe having a barrel defined by a wall and having a first end including a tip and a port through the wall near an opposed second end, and an imperforate plunger configured to be held in a retracted stationary position with all plunger portions that seal to the barrel wall being located between the port and the second end of the barrel to define a volume between the plunger and the first end of the barrel, with the volume being in direct fluid communication with the cell processing system, and an auxiliary container connected to the syringe at the port and in direct fluid communication with the volume and configured to receive a gas displaced from the volume with the plunger held in the retracted stationary position when the syringe receives fluid from the filling system; and
a pump configured to transfer a product from the cell processing system to the at least one filling station.

10. The processing and filling station according to claim 9, wherein the filling system comprises a manifold in fluid communication with the cell processing system, each of the at least one filling stations in fluid communication with the manifold.

11. The processing and filling station according to claim 9, wherein the at least one filling station comprises a clamp to selectively control the flow of fluid to the at least one container, a sensor to monitor the fluid flowing into the at least one container, and a scale configured to monitor the weight of the at least one container.

12. The processing and filling station according to claim 9, wherein the filling station comprises a plurality of filling stations.

13. The processing and filling system according to claim 9, wherein the filing station is in selective fluid communication with the cell processing system and a fluid container, and the pump is configured to transfer a product from the cell processing system and a fluid from the fluid container to the at least one filling station.

14. The processing and filling system according to claim 9, wherein the cell processing system comprises a disposable circuit including the product container and reusable hardware, the circuit and the hardware defining the separator.

15. The processing and filling system according to claim 9, wherein the at least one filling station is in fluid communication with the separator.

16. The processing and filling system according to claim 7, wherein the cell processing system comprises a product container configured to receive one of the at least two streams from the separator, and the at least one filling station is in fluid communication with the product container.

17. The processing and filling system according to claim 16, wherein the volume of the at least one container is at least an order of magnitude smaller than the volume of the product container.

18. The processing and filling system according to claim 9, wherein the syringe is configured as an end-user container.

19. The processing and filling system according to claim 9, wherein when the plunger is in the retracted stationary position, the volume between the plunger and the first end of the barrel is unobstructed.

20. The processing and filling system according to claim 9, comprising a closed disposable circuit including the separator, the syringe, and the auxiliary container.

* * * * *